US006537794B1

(12) United States Patent
Lesslauer et al.

(10) Patent No.: US 6,537,794 B1
(45) Date of Patent: Mar. 25, 2003

(54) CHEMOKINE

(75) Inventors: Werner Lesslauer, Riehen (CH); Ulrike Utans-Schneitz, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/426,326

(22) Filed: Oct. 25, 1999

Related U.S. Application Data

(62) Division of application No. 09/071,353, filed on Apr. 30, 1998, now Pat. No. 6,057,426.

(30) Foreign Application Priority Data

Apr. 30, 1997 (EP) .............................. 97107135

(51) Int. Cl.$^7$ ................... C12N 15/00; C12N 15/09; C12N 15/63; C12N 15/70
(52) U.S. Cl. ................ 435/252.3; 435/320.1; 435/325; 435/252.33; 435/69.1; 435/254.11
(58) Field of Search ................ 530/351, 402, 530/408, 409, 410; 424/85.1; 435/69.1, 320.1, 325, 252.3, 252.33, 254.11

(56) References Cited

U.S. PATENT DOCUMENTS

| 5,194,596 A | * | 3/1993 | Tischer et al. .............. 530/399 |
| 5,602,008 A | | 2/1997 | Wilde et al. | |

FOREIGN PATENT DOCUMENTS

| WO | WO 93/18176 | 9/1993 |
| WO | WO 96/16979 | 6/1996 |
| WO | WO 96/23067 | 8/1996 |
| WO | WO 97/31098 | 8/1997 |
| WO | WO 98/01557 | 1/1998 |
| WO | WO 96/05856 | 2/1998 |
| WO | WO 98/17800 | 4/1998 |
| WO | WO 98/21330 | 5/1998 |

OTHER PUBLICATIONS

Pilbeam et al. Comparison of the Effects of Various Lengths of Synthetic Human Parathyroid Hormone–Related Peptide (hPTHrP) of Malignancy on Bone Resorption and Formation in Organ Culture. Bone 14:717–720 (1993).*
Yan et al. Two–Amino Acid Molecular Switch in an Epithelial Morphogen That Regulates Binding to Two Distinct Receptors. Science 290:523–527 (2000).*
Murdoch et al. Chemokine receptors and their role in inflammation and infectious diseases. Blood vol. 95 No. 10 3032–3043 May 15, 2000.*

Baggiolini, et al., Adv. Immunol., vol. 55, F. J. Dixon, ed., pp. 97–179 (1994).
Strieter, et al., J. Immunol., vol. 156, pp. 3583–3586 (1996).
Rossi, et al., J. Immunol., vol. 158, pp. 1033–1036, (1997).
Hieshima, et al., J. Biol. Chem., vol. 272, pp. 5846–5853, (1997).
Falk, et al., J. Immunol. Meth., vol. 33, pp. 239–247, (1980).
von Tscharner, et al., Nature, vol. 324, pp. 369–372, (1986).
Database EMBL EMROD, Entry RNU90447, Accession No. U90447, XP–002073408, (1997).
Broxmeyer, et al., Human chemokines: enhancement of specific activity and effects in vitro on normal and leukemic progenitors and a factor–dependent cell line and in vivo in mice, Annals of Hematology, vol. 71, No. 5, pp. 235–246 (1995).
Rossi, et. al., Identification Through Bioinformatics of Two New Macrophage Proinflammatory Human Chemokines, Journal of Immunology, vol. 158, No. 3, pp. 1033–1036 (1997).
Hieshima, et al., Molecular Cloning of a Novel Human CC Chemokine Liver and Activation–regulated Chemokine (LARC) Expressed in Liver, Journal of Biological Chemistry, vol. 272, No. 9, pp. 5846–5853 (1997).
Brem, et. al., Interstitial chemotherapy with drug polymer implants for the treatment of recurrent gliomas, Journal of Neurosurgery, vol. 74, No. 3, pp. 441–446 (1991).
Database EMBL EMEST2, Entry AA739063, Accession No. AA739063, XP–002073409 (1998).
Stone, et al. Targeted RNA fingerprinting: the cloning of differentially–expressed cDNA fragmentss enriched for members of the zinc finger gene family, Nucleic Acids Research, vol. 22, No. 13 (1994).
Gonsky, et al., Identification of rapid turnover transcripts overexpressed in thyroid tumors and thyroid cancer cell lines: use of a targeted differential RNA display method to select for mRNA subsets, Nucleic Acids Research, vol. 25, No. 19, pp. 3823–3831 (1997).
Shaw, et al., A Conserved AU Sequence from 3' Untranslated Region of GM–CSF mRNA Mediates Selective mRNA Degradation, Cell, vol. 46, pp. 659–667 (1986).

* cited by examiner

*Primary Examiner*—Elizabeth Kemmerer
*Assistant Examiner*—Regina M. DeBerry
(74) *Attorney, Agent, or Firm*—George W. Johnston; Patricia S. Rocha-Tramaloni; Bernard Lau

(57) ABSTRACT

The present invention relates to the discovery of novel genes and proteins, which function in pathways involved in brain pathogenesis. In particular, the novel genes and proteins relate to inflammatory tissue responses caused by brain injuries such trauma, ischemia or autoimmune-inflammation or other diseases or processes related to neuroinflammation. The compounds disclosed in the present invention are useful as therapeutics, diagnostics and in screening assays.

4 Claims, 11 Drawing Sheets

```
CAGCAGGGCACTGGGTACCCAGCACTGAGCAGATCAATTCCTGGAGCTGAGAATGGCCTG  60
                                                       M  A  C

CAAGCATCTGCCCTTCCTGGCTTTGGCGGGGTACTGCTGGCTTACCTCTGCAGCCAGTC  120
  4 K  H  L  P  F  L  A  L  A  G  V  L  L  A  Y  L  C  S  Q  S

AGAAGCAGCAGCAACTTTGACTGCTGCCTCACGTACACAAAGAACGTGTATCATCATGC  180
 24 E  A* A  S  N  F  D  C  C  L  T  Y  T  K  N  V  Y  H  H  A

GAGAAATTTTGTGGGTTTCACAACAGATGGCCGACGAAGCTTGTGACATTAATGCTAT  240
 44 R  N  F  V  G  F  T  T  Q  M  A  D  E  A  C  D  I  N  A  I

CATCTTTCACCTGAAGTCGAAAAGATCCGTGTGCGCTGACCCAAAGCAGATCTGGGTGAA  300
 64 I  F  H  L  K  S  K  R  S  V  C  A  D  P  K  Q  I  W  V  K

AAGGATTTTGCACCTCCTCAGCCTAAGAACCAAGAAGATGTAAAAACGATGCTTTCTG  360
 84 R  I  L  H  L  L  S  L  R  T  T  K  K  M

GGATGGAATTGGGACACAGCCCAAGGAGGAAATGATCACAGCTGGGGTTGGAGGTTCACC  420

TGCACATCACTGCACAGACCTGATTGTGTCCCAGTGGTCTGTGTCCAATGGATGAAGTTG  480

ATTCATATATTGCATCATATGTGTCATATTTCTATATTTAAGCTCATATTAGAGTTGTATTTTG  540

TGTTATTTATAGATCCGAATTTTCTATGTTTAGCTATTTAATGTTAATTTCCCACAATCT  600

ATGAGGGGCGCTTAGTAGAAGGTTCAATATTATGTTAAGGCAGTAAGTTTATATGCCC  660

TTCTTGGAAACAATAAGCTATTGTAAAAATATTTAATGTTCTTCTGTGTGCTTAATTGTT  720

TCTTAAATTGATACGATTTACTTATAAAACAGAAAGGAATTATAAGAATATATTGAAAAT  780

AAAAGAACTGAAAGGCA
```

FIG. 2a

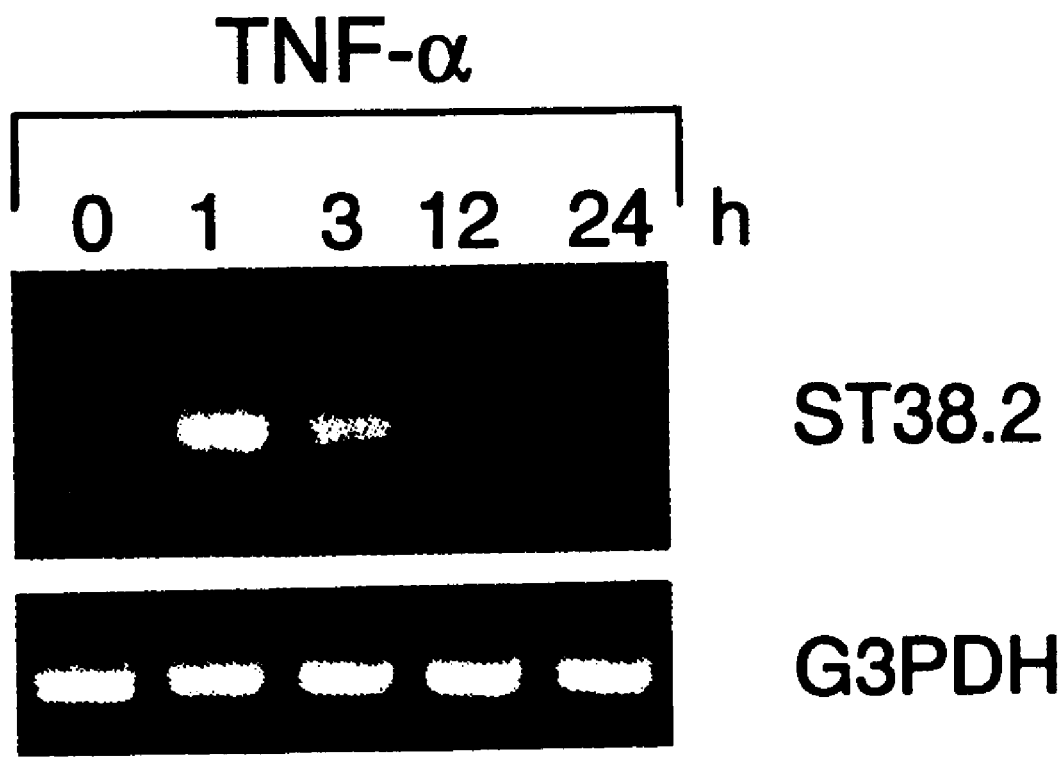
F I G. 7

# CHEMOKINE

CROSS REFERENCE TO RELATED APPLICATION

This is a divisional of application Ser. No. 09/071,353, filed on Apr. 30, 1998, now U.S. Pat. No. 6,057,426.

FIELD OF THE INVENTION

The present invention relates to pro-inflammatory and anti-inflammatory proteins.

BACKGROUND OF THE INVENTION

Brain injury such as trauma, ischemia or autoimmune-inflammation leads to an inflammatory tissue response involving both activated, resident and infiltrating cells. In brain ischemia this inflammatory reaction is characterized by an early influx of polymorphonuclear leukocytes, primarily neutrophils, into the zone of injury followed by a late infiltration of activated microglia and blood monocyte/macrophages (Dereski et al. (1992) Neurosci. Res. Commun. 11:179–186; Ramsay et al. (1992) Lancet 339:1054–1055). Infiltrating leukocytes as well as activated resident glial cells may exert a cytotoxic effector function by releasing reactive oxygen species, nitric oxide, proteinases, inflammatory cytokines or excitotoxins such as glutamate or quinolinic acid and, therefore, have been implicated in the pathogenesis of cerebral ischemia and stroke. (Kochanik & Hallenbeck (1992) Stroke 23:1367–1379; Lees (1993) J. Neurol. Sci. 114:119–122; Wood (1995) Neurol. Res. 17:242:248). The specific mechanisms responsible for the initiation and propagation of the inflammatory reaction in response to focal and transient brain ischemia are not fully elucidated. Studies showing a very early and sustained upregulation of the pro-inflammatory cytokines TNF alpha and IL-1 in the ischemic area and a more delayed increase for mediators such as IL-6, MCP-1 or MIP-1 alpha provide evidence for a specific role of brain cytokines in this process (Buttini et al. (1994) Mol. Brain Res. 23:126–134; Kim et al. (1995) J. Neuroimmunol. 56:127–134; Wang et al. (1995) Stroke 26: 661–666; Buttini et al. (1996) Neurosci. 71:1–16; Yoshimoto et al. (1997) Acta Neuropathol. 93:154–158).

The molecular mechanism of inflammatory cell infiltration involves a complex series of adhesive interactions between circulating leukocytes and vascular endothelium adjacent to the inflammatory site mediated by locally produced pro-inflammatory cytokines and chemoattractants (Butcher (1991) Cell 67:1033–1036; Carlos & Harlan (1994) Blood 84:2068–2101). Among the chemoattractants, chemokines are a family of small cytokines thought to mediate the directional migration of specific target populations of leukocytes along concentration gradients through the endothelial cell layer to the site of lesion (Baggiolini et al. (1994) Adv. Immunol. 55: 97–179). This cascade of events, however can display a high degree of specificity in relation to the inflammatory stimulus, the stage of the inflammatory response and the tissue or organ involved (Butcher et al., loc. cit.).

The family of chemokines can be subdivided in two main groups based on the position of the first two of four conserved cysteine residues which are separated by a single amino acid residue in the CXC family of chemokines or juxtaposed in the CC family (Baggiolini et al., loc. cit.; Strieter et al. (1996) J. Immunol. pp. 3583–3586). In general, CXC chemokines are potent chemoattractants for neutrophils whereas CC chemokines act on monocytes but also on basophils, eosinophils and T-lymphocytes. Recently several novel CC chemokines have been discovered by homology searches in EST databases (Rossi et al., (1997) J. Immunol., 158: 1033–1036; Hieshima et al. (1997) J. Biol. Chem., 272:5846–5853). The biological role of these proteins as well as their physiological functions remains to be determined.

SUMMARY OF THE INVENTION

The present invention is based on the discovery of novel polypeptides, referred to herein as the "ST38.2" polypeptides, which function as chemokines related to inflammatory and immune responses, particularly related to neuroinflammatory responses.

In accordance with the present invention ST38.2 polypeptides are encoded by nucleic acid molecules comprising nucleic acid molecules selected from (a) a nucleic acid molecule or a complement of a nucleic acid molecule set forth in SEQ ID NO:1;

b) a nucleic acid molecule or a complement of a nucleic acid molecule encoding a polypeptide set forth in SEQ ID NO:2 or SEQ ID NO:3;

(c) a nucleic acid molecule capable of hybridizing to a nucleic acid molecule of (a) or (b); and (d) a nucleic acid encoding variations, homologues, derivatives or fragments of the polypeptides defined by (a), (b) or (c).

Some ST38.2 polypeptides possess the pro-inflammatory activities of inducing migration of leukocytes and/or activating leukocytes in a dose-dependent manner. These polypeptides are useful for increasing cell layer permeability to allow drugs to circulate to their respective targets, which is desirable in treating tumors and infectious diseases. These peptides are important mediators in host defense, and can be used as part of wound healing therapy. Polypeptides which activate leukocytes are also useful for treating tumors since activated leukocytes can kill or inhibit tumors. Other ST38.2 polypeptides are agonists of chemotaxis and/or leukocyte activation, possess anti-inflammatory activity and are useful in the treatment of inflammatory or immune diseases.

DESCRIPTION OF FIGURES

FIG. 2A: Nucleotide sequence of the rat ST38.2 cDNA. Nucleotide sequence and deduced amino acid sequence of the rat ST38.2 cDNA (SEQ ID NO: 2). Nucleotide numbering in FIG. 2 is shown on the left. The asterisks indicates the putative cleavage site of the signal peptidase. Underlined are five repeats of the AUUUA motif located in the 3' untranslated region. The double underlined sequence indicates a polyadenylation signal.

FIG. 7: Expression of ST38.2 transcripts in primary astrocyte cultures. cDNA was prepared from astrocytes stimulated for the indicated time periods with TNF-alpha (100 ng/ml) and PCR amplified with ST38.2 primers F2/B2 for 40 cycles. PCR reactions were analyzed on ethidium-stained agarose gels. To show equal template concentration in all samples, cDNAs were amplified with primers for G3PDH.

DETAILED DESCRIPTION OF THE INVENTION

Figure 1A:
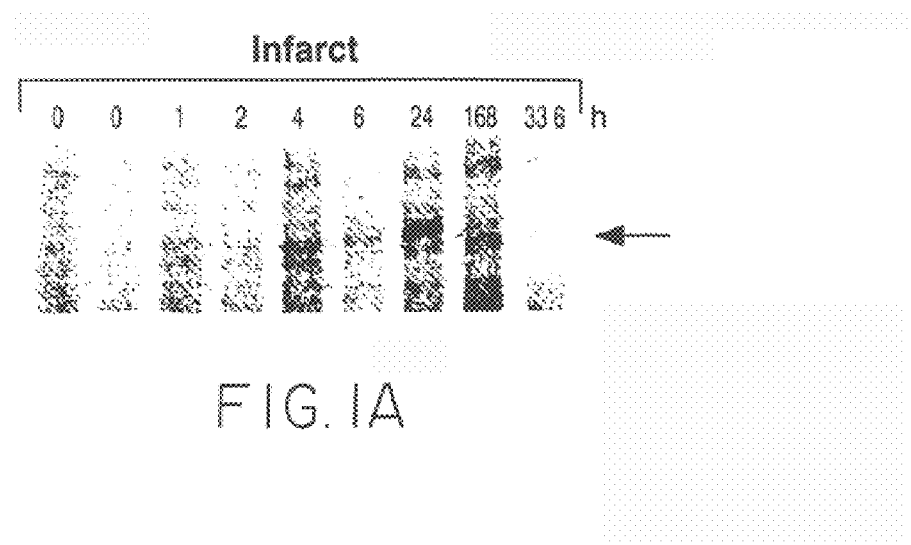
FIG. 1A: Identification of a differentially regulated transcript in infarct tissue. Total RNA was extracted from infarct core tissue harvested at the indicated time points following MCAO, reverse transcribed and subjected to differential display analysis using primers 5'-GTCTTGTATTTATTTATTTAT-3' (SEQ ID NO:5) and 5'-GCTCTAGAT$_{16}$-3' (SEQ ID NO:4). $^{33}$P-labeled PCR products were resolved on a 6% denaturing gel and visualized by autoradiography. The display band upregulated in the 4, 6, and 24 hour lanes (arrow) was recovered from the gel, reamplified and subcloned.

The term "ST38.2 polypeptide" or "ST38.2 protein" includes in its most basic form polypeptides comprising an ST38.2 polypeptide amino acid sequence derived from the core region which in the appropriate conditions is capable of displaying chemotactic activity and is capable of activating leukocytes in a dose-dependent manner, especially relevant for neuroinflammatory reactions in the brain.

Especially, the present invention provides ST38.2 polypeptides encoded by nucleic acid molecules comprising nucleic acid molecules selected from
 (a) a nucleic acid molecule or a complement of a nucleic acid molecule set forth in SEQ ID NO:1;
 (b) a nucleic acid molecule or a complement of a nucleic acid molecule encoding a polypeptide set forth in SEQ ID NO:2 or SEQ ID NO:3;
 (c) a nucleic acid molecule capable of hybridizing to a nucleic acid molecule of (a) or (b); and
 (d) a nucleic acid encoding variations, homologues, derivatives or fragments of the polypeptides defined by (a), (b) or (c);
wherein the ST38.2 protein retains chemotactic activity and is capable of activating leukocytes in a dose-dependent manner. This invention also provides ST38.2 antagonist polypeptides encoded by nucleic acid molecules as described above, which inhibit or downregulate the chemotactic and/or leukocyte activating activities of pro-inflammatory ST38.2 proteins.

In an embodiment this invention provides ST38.2 polypeptides encoded by nucleic acid molecules comprising nucleic acid molecules selected from
 (a) a nucleic acid molecule or a complement of a nucleic acid molecule set forth in SEQ ID NO:1;
 (b) a nucleic acid molecule or a complement of a nucleic acid molecule encoding a polypeptide set forth in SEQ ID NO:2 or SEQ ID NO:3; and
 (c) a nucleic acid molecule capable of hybridizing to a nucleic acid molecule of (a) or (b),
wherein the ST38.2 protein retains chemotactic activity and is capable of activating leukocytes in a dose-dependent manner.

The term "ST38.2 polypeptide" or "ST38.2 protein" comprises variations, homologues, derivatives or fragments which display one or more biological activities of a wild-type ST38.2 polypeptide, e.g., the murine or human ST38.2 polypeptide.

The terms "biological activity" or "bioactivity" of ST38.2 proteins refers to their chemotactic activity and their ability to activate leukocytes in a dose-dependent manner, especially to clinical recruitment and activation of inflammatory cells including activation of resident immune competent cells related to neuroinflammatory processes. The measurement of chemotactic activity is known in the art and may be determined by measurement of leukocyte migration as described by Falk et al. (1980) J. Immunol. Meth. 33:239–247. Leukocyte activation may be measured by methods known in the art, for example by determination of intracellular free calcium concentration as for instance described by von Tscharner et al. (1986) Nature 324:369–372.

The terms "modulation" and "modulate" as used herein refers to both upregulation, i.e., stimulation, and downregulation, i.e. suppression of a response.

The invention also makes available isolated ST38.2 polypeptides which are isolated from, or otherwise substantially free of other cellular proteins. The term "substantially free of other cellular proteins" or "substantially pure or purified preparations" are defined as encompassing preparations of ST38.2 polypeptides of less than 20% (by dry weight) contaminating protein, and preferably having less than about 5% contaminating proteins.

In preferred embodiments, purified ST38.2 preparations will lack any contaminating proteins from the cells from which ST38.2 normally is produced, as can be accomplished by recombinant expression of, for example a human ST38.2 polypeptide in a non-human cell.

Homology will be at least about 50%, generally at least 60%. Homologous proteins or peptides, such as allelic variants, will share most biological activities with the embodiments set forth in SEQ ID NO:2 or SEQ ID NO:3, i.e., these compounds retain chemotactic activity and are capable of activating leukocytes in a dose-dependent manner as mentioned above. For example, ST38. 2 polypeptides can be encoded by all or a portion of nucleic acid sequence set forth in SEQ ID NO:1 (rat ST38.2 cDNA). Amino acid homology, or sequence identity, is determined by optimizing residue matches, if necessary, by introducing gaps as required (Needleham et al. (1970) J. Mol. Biol. 48:443; Sankoff et al., chapter one in "Time Warps, String Edits, and Macromolecules: The Theory and Practice of Sequence Comparison") 1983, Addison-Wesley, Reading, Mass.).

Moreover, it will be generally appreciated that, under certain circumstances, it may be advantageous to provide homologues of the ST38.2 polypeptides which function in a limited capacity as one of either a ST38.2 agonist (mimetic) or a ST38.2 antagonist, in order to promote or inhibit only a subset of the biological activities of the naturally occurring forms of the protein. Thus, specific biological effects can be elecited by treatment with a homologue of limited function, and with fever side effects relative to treatment with agonists or antagonists which are directed to all of the biological activities of naturally occurring forms of ST38.2 polypeptides.

Homologues of the polypeptides of the invention can be generated by mutagenesis, such as by discrete point mutation(s) or by truncation. For instance, mutation can give rise to homologues which retain substantially the same, or merely a subset, of the biological activity of the ST38.2 polypeptide from which it is derived. Alternatively, antagonistic forms of the polypeptide can be generated which are able to inhibit the function of the naturally occurring form of the protein, such as by competitively binding to a downstream or upstream member of biochemically pathway which includes the ST38.2 polypeptide. In addition, agonistic forms of the protein may be generated which are constitutatively active.

ST38.2 polypeptides include allelic variations and, in addition, homologues of the wild-type polypeptides, such as versions of those polypeptides which are resistant to proteolytic cleavage, as for example, due to mutations which alter ubiquitination or other enzymatic targeting associated with the protein.

In an embodiment, the ST38.2 polypeptide is a mature polypeptide. As used herein, the terms mature polypeptide" or ,mature protein" refer to naturally occurring or recombinant proteins which have undergone post-translational modification (e.g., cleavage of a leader sequence).

In a preferred embodiment, the invention provides vertebrate ST38.2 polypeptides, preferably murine and human ST38.2 polypeptides and most preferably the mature form of murine or human ST38.2. For example, the amino acid sequence of translated rat ST38.2 polypeptide is shown in FIG. 2a and in SEQ ID NO:2. The amino acid sequence of mature rat ST38.2 polypeptide (i.e., after cleavage of the leader sequence) is shown in SEQ ID NO:3.

The mature form of the rat ST38.2 protein (SEQ ID NO:3) is characterized by an apparent molecular weight of $8.2 \pm 2$ kD, which may be determined by SDS page gel electrophoresis. It will be understood that certain post-translational modifications, e.g., glycosilation and the like, can increase the apparent molecular eight of the ST38.2 protein relative to the unmodified polypeptide.

The present invention further pertains to recombinant ST38.2 polypeptides. Such recombinant ST38.2 polypeptides preferably are capable of functioning in one of either role of an agonist or antagonist of at least one biological activity of the wild-type protein of SEQ ID NO:2 or SEQ ID NO:3, respectively.

Isolated portions of ST38.2 polypeptides (fragments) can be obtained by screening peptides recombinantly produced form the corresponding fragment of the nucleic acid encoding such peptides. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments which can function as either agonists or antagonists of a wild-type ST38.2 polypeptide.

Derivatives and/or modifications of ST38.2 polypeptides are included within the scope of this invention. These terms comprise for example chemical modifications (derivatives) which may be prepared from the functional groups occurring as side chains on the residues or the N- or C-terminal groups, by means known in the art. These derivatives may include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl groups (for example that of seryl- or threonyl residues) formed with acyl moieties. ST38.2 polypeptides may be linked to one of a variety of non-proteinaceous polymers, e.g., polyethylene glycol, polypropylene glycol, or other polyalkylenes which may be branched or unbranched. The polymers may be directly linked to the polypeptide or may be linked by means of linking groups connecting for example the COOH of a polymer to the $NH_2$ of a lysine on the polypeptide. In general, these type of derivatives also include other chemical modifications by forming covalent or aggregate conjugates with other chemical moieties, such as glycosyl groups, lipids, phosphate, acetyl groups and the like.

The terms "derivatives and/or modifications" of "ST38.2 polypeptide" or "ST38.2 protein" further includes amino acid sequence derivatives (modifications) enhancing therapeutic or prophylactic efficacy, stability, or post-translational modifications. These derivatives can be produced, for instance, by amino acid substitution, and/or deletion, and/or addition. For example, it is reasonable to expect that an isolated replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Whether one or more changes in the amino acid sequence of a polypeptide results in a polypeptide with ST38.2 bioactivity can be readily be determined by assessing the ability of the variant to produce a response in cells in a fashion similar to a wild-type ST38.2 polypeptide.

Fusion proteins between the ST38.2 polypeptides and other homologous or heterologous proteins are also provided. Homologous polypeptides may be fusions between different chemokines, resulting in, for instance, a hybrid protein exhibiting ligand specificity for multiple different receptors, or a ligand which may have broadened or weakened specificity of binding to its receptor. Likewise, heterologous fusions may be constructed which would exhibit a combination of properties or activities of the derivative proteins. For example, a fusion protein can comprise a ST38.2 polypeptide as defined above and a second polypeptide which is a detectable label, e.g., a reporter protein, e.g., luciferase.

A further aspect of the invention pertains to nucleic acids comprising nucleotide sequences or nucleic acid molecules encoding ST38.2 polypeptides mentioned above, and/or equivalents of such nucleic acids. The term "nucleic acid" refers to polynucleotides such as deoxyribonucleic acid (DNA), and, where appropriate, ribonucleic acid (RNA). The term should also be understood to include, as equivalents, analogs of either RNA or DNA made form nucleotide analogs, single (sense or antisense) and double-stranded polynucleotides.

The term "nucleic acid" is understood to include nucleotide sequences encoding functionally equivalent ST38.2 polypeptides or functionally equivalent polypeptides having an activity of a ST38.2 polypeptide such as described herein. These nucleic acid molecules will include sequences that differ by one or more nucleotide substitution, addition or deletion, such as allelic variants; and will therefore, include sequences that differ from the nucleotide sequence of the ST38.2 gene shown in SEQ ID NO:1 due to the degeneracy of the genetic code.

Preferred nucleic acids are vertebrate ST38.2 nucleic acids. Particularly preferred vertebrate acids are mammalian. Regardless of species, particularly preferred nucleic acids encode polypeptides that are at least 50% similar to an amino acid sequence of a vertebrate polypeptide, preferably the amino acid sequence shown in SEQ ID NO:2 or SEQ ID NO:3. Most preferably, the nucleic acid includes all or a portion of the nucleotide sequence corresponding to the nucleic acid of SEQ ID NO:1 or the corresponding human sequence or complements thereof.

Still other preferred nucleic acids of the present invention encode the mature form of the ST38.2 polypeptide.

Another aspect of the invention provides a nucleic acid which is capable of hybridizing to a nucleic acid shown in SEQ ID NO:1 or to a nucleic acid capable of hybridizing to a nucleic acid which encodes the polypeptide of SEQ ID NO:2. Appropriate stringency conditions which promote DNA hybridization, for example 6.0×sodium chloride/sodium citrate (SSC) at about 45° C., followed by a wash of 2.0×SSC at 50° C., are known to those skilled in the art or can be found in "Current Protocols in Molecular Biology", John Wiley & Sons, NY (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a ST38.2 nucleic acid of the present invention will bind to the nucleic acid of SEQ ID NO:1 under low to moderately stringent conditions, for example at about 2.0× SSC and about 40° C. For example, nucleic acid of SEQ ID NO:1 will bind under low stringent conditions to its human analog (Example 5).

Preferred nucleic acids have a sequence at least 50% homologous and more preferably 55% and even more preferably at least 60% homologous with an amino acid sequence of a ST38.2 gene, e.g., such as the sequence shown in SEQ ID NO:2. In preferred embodiments, the nucleic acid is a vertebrate nucleic acid, preferably mammalian, and in particularly murine or human.

As indicated by the examples set out below, ST38.2 protein-encoding nucleic acids can be obtained from mRNA present in any of a number of eukaryotic cells. It should also be possible to obtain nucleic acids encoding ST38.2 polypeptides of the present invention from genomic DNA. For example, a gene encoding a ST38.2 polypeptide can be cloned from either a cDNA or a genomic library in accordance with protocols described herein, as well as those generally known to persons skilled in the art. Examples of tissues and/or libraries thereof for isolation of suitable nucleic acids include those of lung and thymus, among others. A cDNA encoding a ST38.2 protein can be obtained by isolating total mRNA from a cell, e.g., a vertebrate cell, preferably a human cell. Double stranded cDNA can then be prepared from the total mRNA, and subsequently inserted into a suitable plasmid or bacteriophage vector using any one of a number of known techniques. The gene encoding a ST38.2 polypeptide can also be cloned using established polymerase chain reaction techniques in accordance with the nucleotide sequence information provided by the invention. The nucleic acid of the invention can be DNA or RNA or analogs thereof. A preferred nucleic acid is a cDNA represented by a human cDNA or the nucleic acid represented by SEQ ID NO: 1.

According to the present invention, the cloning of ST38.2 polypeptides may also be performed by identification of a transcriptionally upregulated gene in ischemic tissue by differential display using biased primer design (Examples 1 to 5). In its original form differential display is an unbiased, PCR-based technique that allows to compare complex transcript expression patterns between different cell populations or tissue samples (Liang et al., loc. cit.). To narrow down the range of genes into a preselected population with high probability to be relevant in the disease context under study, the screen was focused on a specific subset of genes that contain AU-rich sequence elements in their 3' untranslated region.

Accordingly, a further embodiment of the present invention comprises a modified differential display method. This method for the isolation of cDNAs of interest comprises (a) preparation of cDNA by transcription of the mRNA of interest, (b) amplification of specific cDNA by polymerase chain reaction based on at least one primer containing one or more consensus elements of the genes of interest, and, if desired, (c) completion of the cDNA of step (b). In a preferred embodiment, the mRNA of interest is isolated after induction of the biochemical pathway, disease or pathological symptom of interest. The method especially refers to the screening of genes related to neuroinflammatory processes and is described in detail in the Examples.

In general, the technique is based on the screening of a specific subset of genes containing sequence elements characteristic for genes of interest, e.g., AU-rich sequence elements being characteristic for genes related to the neuroinflammatory pathways and/or diseases. The subset of genes may be prepared by isolation of mRNA of cells of interest, reverse transcription and amplification, preferably by polymerase chain reaction. The cells may be induced before mRNA isolation to stimulate the transcription of the genes of interest, e.g., for the isolation genes related to neuroinflammatory processes and pathways by inducing ischemic injury by permanent middle cerebral artery occlusion (MCAO) as described in Example 1. The resulting amplified DNA's may be completed by methods known in the art, e.g., 5' or 3' RACE amplification as described in the examples.

Figure 1B:
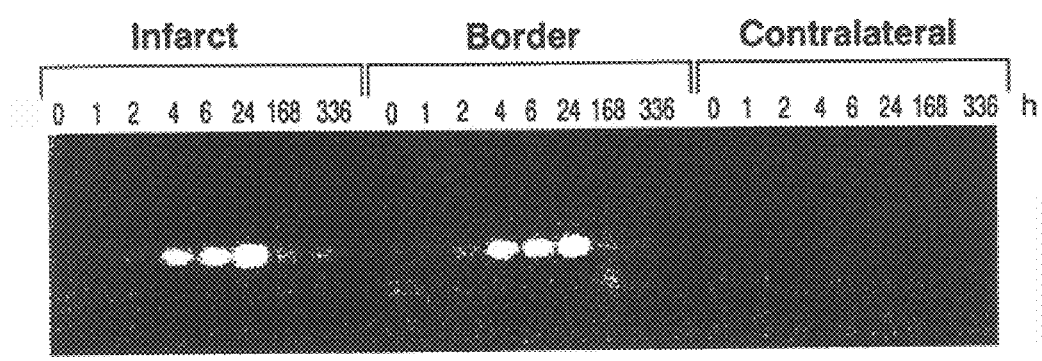
FIG. 1B: Identification of a differentially regulated transcript in infarct tissue. RT-PCR analysis confirming the time-dependent gene induction in infarct tissue. cDNAs (1.25 μl) of infarct core, border zone and contralateral tissue were PCR amplified using primers annealing to the subcloned differential display cDNA fragment, termed ST38.2 for 30 cycles. To show equal template concentration in all samples, cDNAs were amplified with primers for G3PDH.
Figure 1C:
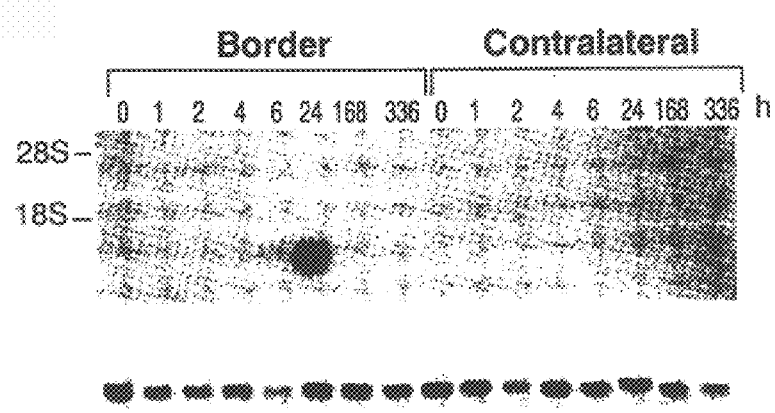
FIG. 1C: Identification of a differentially regulated transcript in infarct tissue. Northern blot analysis. Total RNA obtained from border zone and contralateral tissue was hybridized with the $^{32}$P-labeled differential display cDNA fragment. Transcripts of 0.8 kb hybridized to the cDNA probe demonstrating an increase in expression from 4 h to 24 h in border zone tissue but not in contralateral tissue. RNA loading was evaluated by rehybridizing the same blot with a G3PDH probe.

A modified PCR-based differential display screen selectively targeting a subset of genes exhibiting AU-rich consensus elements was performed to identify genes potentially active during the neuroinflammatory reaction associated with brain ischemic injury. Ischemia was induced by permanent MCAO and animals were sacrificed at different times after MCAO. Total RNA was extracted from infarct core, border zone and contralateral tissue and reverse transcribed into first strand cDNA. Differential display PCR amplification was carried out using a $(ATTTA)_3$ primer containing a six-nucleotide anchor at the 5' end in combination with an oligo dT primer and the PCR products were analyzed by electrophoresis and autoradiography. Comparing the PCR amplification products of infarct core cDNA from various time points with those of untreated controls one differential display band, termed ST38.2 was identified, that was present in increasing concentrations in the 4, 6 and 24 hour infarct lanes but absent at other time points or in the control tissue (FIG. 1A). The ST38.2 band was recovered from the gel, reamplified and subcloned. The differential regulation observed on the display gel was first confirmed by RT-PCR using ST38.2-specific PCR primers (FIG. 1B). The RT-PCR analysis demonstrated the upregulation of ST38.2 transcripts in the infarct core with a peak of expression at 24 hours after ischemia. The same time-dependent pattern of expression was found in border zone tissue whereas no expression could be detected in untreated control tissues or on the contralateral side. In a second approach the ST38.2 differential display cDNA fragment of 291 bp was used as a probe for northern blot analysis of MCAO border zone and contralateral tissue (FIG. 1C). A strongly hybridizing band of 0.8 kb could be detected in the border zone at 24 h and to a lesser extent at 6 and 4 h, but not in contralateral or control tissue, again confirming the transient, time-dependent upregulation of this transcript in ischemic tissue.

Figure 2B:
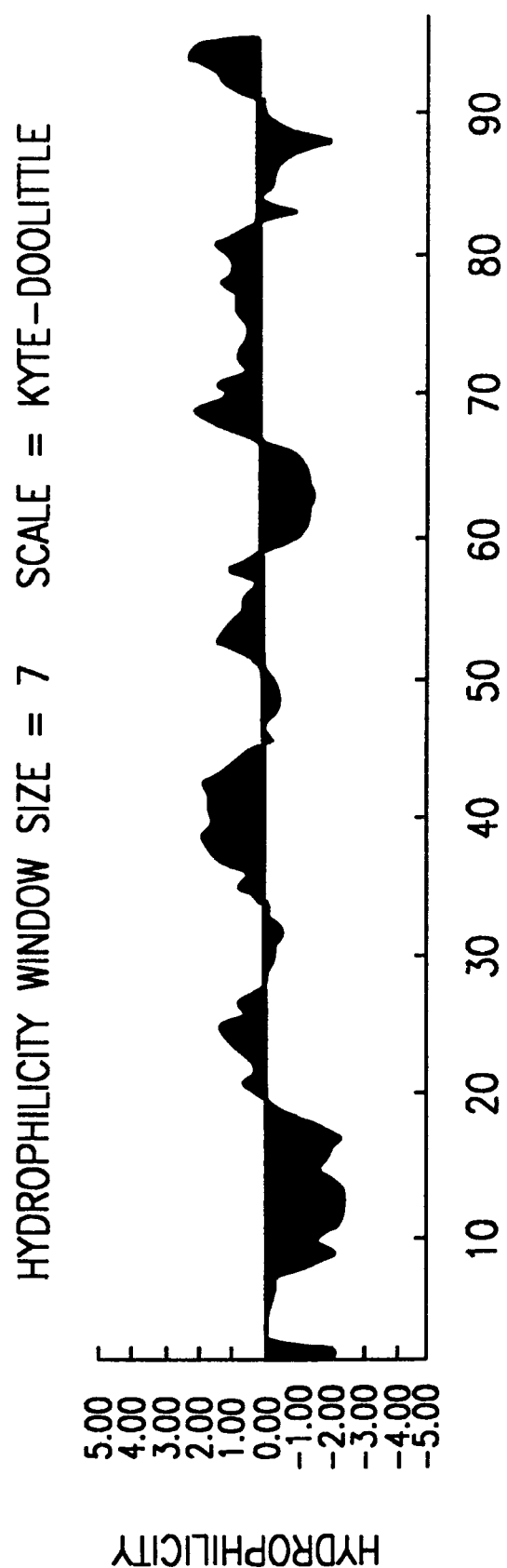
FIG. 2B: Hydrophilicity plot of the deduced amino acid sequence showing a hydrophobic leader sequence at the N-terminus.

The ST38.2 cDNA fragment isolated by differential display is derived from the 3' end of the gene and did not contain an open reading frame. To obtain a 5' extended sequence, a 5' RACE reaction was performed. The sequence obtained from several RACE clones is 797 bp long which is similar to the size of the transcript detected by Northern blot hybridization (FIG. 2A). The sequence contains an open reading frame which can be translated in a polypeptide of 97 amino acids. The N-terminus of the deduced amino acid sequence encodes a hydrophobic leader sequence characteristic of secreted proteins with a predicted cleavage site at position 25 (FIG. 2B). The mature protein has a predicted size of 8.2 kD and a pI of 9.96. The 3' untranslated sequence includes a potential polyadenylation signal and five single ATTTA sequences. The differential display primer targeted a sequence that contained one of these ATTTA sequences embedded in a T-rich stretch.

A search for known polypeptide motifs within the ST38.2 sequence indicated that the protein belongs to the class of C—C chemokines. Homology searches of the ST38.2 cDNA sequence revealed 75% identity on nucleotide level and 61% identity on amino acid level to the recently identified human C—C chemokine termed MIP-3 alpha or LARC (Rossi et al. (1997) J. Immunol. 158:1033–1036); Hieshima et al. (1997) J. Biol. Chem. 272:5846–5853).

The cDNA obtained can be inserted in an appropriate vector, either for preparation of large quantities of nucleic acids for further processing (cloning vectors) or for expression of the ST38.2 polypeptide (expression vectors).

Vectors, as used herein, comprise plasmids, viruses, bacteriophages, integratable nucleic acid fragments, and other vehicles which enable the integration of nucleic fragments into the genome of the host. Plasmids are the most commonly used form of vector but all other forms of vectors which serve an equivalent function and which are, or become, known in the art are suitable for the use herein. Cloning vectors need not contain expression control sequences. However, control sequences are needed in an expression vector, and these control sequences include transcriptional and translational control sequences such as a transcriptional promoter, an optional operator sequence to control transcription, a sequence encoding suitable ribosome binding sites (for prokaryotic expression), and sequences which control termination of transcription and translation. The expression vector should preferably include a selection gene to facilitate the stable expression of ST38.2 polypetides and/or to identify transformants. However, the selection gene for maintaining expression can be supplied by a separate vector in cotransformation systems using eukaryotic host cells.

The vectors of this invention include those which contain a nucleic acid which encodes a polypeptide, as described, or a fragment thereof encoding a biologically active equivalent polypeptide. This nucleic acid can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question.

As used herein, "expression vector" refers to a vector such as plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in various eukaryotic expression systems preferably include a signal sequence enabling extracellular secretion of translated protein by a host cell.

Alternatively, where recombinant protein is expressed without a signal or transport sequence, it may include an N-terminal methionine residue. This residue may optionally be subsequently cleaved from the expressed recombinant protein to provide a final product.

Usually, expression vectors are designed for stable replication in their host cells or for amplification to greatly increase the total number of copies of the desirable gene per cell. It is not always necessary to require that an expression vector replicates in a host cell, e.g., it is possible to effect transient expression of the ST38.2 polypeptide or its fragments, homologues or variants in various host using vectors that do not contain a replication origin that is recognized by the host cell. It is also possible to use vectors that cause integration of the ST38.2 polypeptide gene into the host DNA by recombination.

Host cells are transformed cells, preferably mammalian, that have been transformed or transfected with vectors constructed using recombinant DNA techniques. Transformed host cells usually express the desired polypeptide or its fragments, but for purposes of cloning, amplifying, and manipulating its nucleic acids, do not need to express the subject protein. This invention further contemplates culturing transformed cells in a nutrient medium, thus permitting a ST38.2 polypeptide to accumulate in the culture. The polypeptide can be recovered, either from the culture or from the culture medium.

Nucleic acids may operably linked when they are functionally related to each other. For example, a promoter is operably linked to a coding sequence if it controls the transcription of the polypeptide; a ribosome binding site is operably linked to a coding sequence if it is positioned to permit translation.

Suitable host cells include prokaryotic and lower and higher eukaryotic cells. Prokaryotes include Gram negative or Gram positive organisms, e.g., *E. coli* and *B. subtilis*. Eukaryotic cells include yeast, baculovirus or higher eukaryotic cells such as established cell lines of mammalian origin.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express the ST38.2 polypeptide and its derivatives include for example vectors containing the lac promoter (pUC-series); trp promoter (pBR322-trp); Ipp promoter (the pIN-series), lambda-pP or pR promotors (pOTS), or hybrid promoters such as ptac (pDR540) (Brosius et al. in "Vectors: A Survey of Molecular Cloning Vectors and Their Uses", (eds. Rodriguez and Denhardt), 1988, Buttersworth, Boston, pp. 205–236).

Lower eukaryotes, e.g., yeasts, may be transformed with ST38.2 containing vectors. For purposes of this invention, the most common lower eukaryotic host is *Saccharomyces cerevisiae*. It will be used to generically represent lower eukaryotes although a number of other strains and species are also available. Yeast vectors typically consist of a replication origin (unless of the integrating type), a selection marker, a promoter, DNA encoding the ST38.2 polypeptide, and sequences for translation termination, polyadenylation, and transcription termination. Suitable expression vectors for yeast include such constitutive promotors as 3-phosphoglycerate kinase and various other glycolytic enzyme gene promotors or such inducible promotors as the alcohol dehydrogenase 2 promoter or metallothionine promoter. Suitable vectors include derivatives of the following types: self-replicating low copy number, self-replication high copy number, integrating types or mini-chromosomes.

Higher eukaryotic tissue culture cells are normally the preferred host cells for expression of the functionally active ST38.2 polypeptide. In principle, any higher eukaryotic tissue culture cell line is workable, e.g., insect baculovirus expression systems, whether from an invertebrate or vertebrate source. However, mammalian cells are preferred. Examples of useful cell lines include HeLa cells, CHO cell lines, BRK cell lines, insect cell lines, bird cell lines and COS cell lines. Expression vectors for such cell lines usually include an origin of replication, a promoter, translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promotors derived, e.g., from such sources as from adenovirus, SV40, parvoviruses, vaccinia virus, or cytomegalovirus. Representative examples of suitable expression vectors include pcDNA1, pCD (Okayama et al. (1985) Mol. Cell. Biol. 5:1136); pMC1neo PolyA (Thomas et al. (1987) Cell 51:503), and a baculovirus vector such as pAC 373 or pAC 610.

If it is desired to express the ST38.2 polypeptide in a system which provides a specific or defined glycosylation pattern, the usual pattern will be that provided naturally by the expression system. However, the pattern will be modifiable by exposing the polypeptide, e.g., an unglycosylated form, to appropriate glycosylating proteins introduced into a heterologous expression system.

Accordingly, the invention also refers to methods of preparation of ST38.2 polypeptides. If prepared by recombinant methods, a process for preparation comprises the steps of (a) culturing appropriate host cells in a culture medium to produce a ST38.2 polypeptide, and (b) isolating the ST38.2 polypeptide.

Based on the known amino acid sequence, ST38.2 polypeptides may be prepared by conventional methods of peptide synthesis, e.g., solid phase synthesis methods (Merrifield et al. (1963) J. Am. Chem. Soc. 85:2149,; Bodansky et al. "The Practice of Peptide Synthesis", 1984, Springer-Verlag, NY; Steward et al., "Solid Phase Peptide Synthesis", 1984, Pierce Chemical Com., Rockford, Ill.).

ST38.2 polypeptides prepared by chemical or recombinant methods may be recovered in accordance with known procedures. Preferably, an expression vector will be used which provides for secretion of ST38.2 polypeptides from the host cells; thus the cells may be separated by centrifugation. ST38.2 is typically purified by general protein purification techniques, including, but not limited to, size exclusion, ion-exchange chromatography, HPLC, and the like. For example the polypeptides may be purified by immuoaffinity chromatography using antibodies directed against an ST38.2 polypeptide.

Accordingly, yet another aspect of the present invention pertains to an antibody specifically reactive with a ST38.2 polypeptide. Besides for purification processes, these antibodies, including both polyclonal and monoclonal antibodies, may possess certain therapeutic applications and may thus be utilized for the purpose of treating the effects of the biological activity of ST38.2 polypeptides, such as neuroinflammation. For instance, the antibodies can be screened for binding to normal or defective ST38.2 polypeptides, or screened for agonistic or antagonistic activity.

For example, by using immunognes derived from a ST38.2 polypeptide, e.g., based on the cDNA sequences, anti-polypeptide antisera or monoclonal antibodies can be made by standard protocols (e.g., "Antibodies: A Laboratory Manual" ed. by Harlow and Lane, Cold Spring Harbor Press (1988)). A mammal, such as a mouse or a rabbit can be immunized with an immunogenic form of the peptide (e.g., a mammalian ST38.2 polypeptide or antigenic fragment which is capable of eliciting an antibody response, or a fusion protein as described above). Following immunization of an animal with an antigenic preparation of a ST38.2 polypeptide, anti-ST38.2 antisera can be obtained and, if desired, polyclonal anti-ST38.2 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art (Kohler & Milstein (1975) Nature 256:495–497; Kozbar et al. (1983) Immunology Today, 4:72; Cole et al. (1985) "Monoclonal Antibodies and Cancer Therapy", Alan R. Liss Inc. pp. 77–96).

The term "antibody" as used herein is intended to include fragments thereof which are also specifically reactive with the ST38.2 polypeptides. Antibodies can be fragmented using conventional techniques and the fragments screened for utility in the same manner for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain and chimeric molecules having affinity for a ST38.2 polypeptide conferred by at least one CDR region of the antibody. In preferred embodiments, the antibody further comprises a label attached thereto and able to be detected, (e.g., the label can be an radioisotope, fluorescent compound, enzyme or enzyme co-factor, inhibitors, chemoluminiscent moieties, magnetic particles etc.;). Patents teaching the use of such labels include U.S. Pat. Nos. 3,817,837; 3,850,752; 3,939,350; 3,996,345; 4,277,437; 4,275,149; and 4,366,241.

Antibodies which specifically bind ST38.2 epitopes can also be used in immunohistochemical staining of tissue samples in order to evaluate the abundance and pattern of ST38.2 expression. Anti-ST38.2 antibodies can be used diagnostically in immuno-precipitation and immuno-blotting to detect and evaluate ST38.2 polypeptide levels in tissue as part of a clinical testing procedure, e.g., for predictive valuations of the onset or progression of proliferative disorders. The antibodies of this invention may be administered by known methods to relieve conditions caused by the presence of ST38.2 polypeptides. In particular, the antibodies of this invention are useful in reducing neuroinflammation and can be administered, for example, for the purpose of suppressing neuroinflammatory or immune responses in a human.

Antibodies directed against ST38.2 polypeptides as defined above, may also be used in disease diagnostics and prognostics. Such diagnostic methods, may be used to detect abnormalities in the level of protein expression, or abnormalities in the structure and/or tissue, cellular, or subcellular location of a protein. Protein from the tissue, e.g., brain, or cell type to be analyzed may easily be detected or isolated using techniques which are well known in the art, including but not limited to western blot analysis (see for example Harlow and Lane, loc. cit.). This can be accomplished, for example, by immunofluorescence techniques employing a fluorescently labeled antibody coupled with light microscopic, flow cytometric, or fluorimetric detection. The antibodies usefull in the present invention may, additionally, be employed histologically, as in immunofluorescence or immunoelectron microscopy, for in situ detection of proteins.

Often a solid phase support or carrier is used as support capable of binding the compounds (antigens) of a sample. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Preferred supports include polystyrene beads.

One means for labeling an antibody is via linkage to a reporter molecule, e.g., an enzyme in an enzyme immunoassay (ELISA) or fluorophores. The visible signal of the reporter molecule is used to indicate the binding of the presence of the ST38.2 polypeptide.

By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others.

The substrates to be used with the specific enzymes are generally chosen for the production, upon hydrolysis by the corresponding enzyme, of a detectable colour change. For example, p-nitrophenyl phosphate is suitable for use with alkaline phosphatase conjugates; for peroxidase conjugates, 1,2-phenylenediamine or tetramethylbenzidine are commonly used. It is also possible to employ fluorogenic substrates, which yield a fluorescent product rather than the chromogenic substrates noted above. In all cases, the enzyme-labelled antibody is added to the corresponding sample and allowed to bind to the ST38.2 polypeptide, then the excess reagent is washed away. A solution containing the appropriate substrate, hydrogen peroxide, is then added to the tertiary complex of antibody-antigen-labelled complex. The substrate reacts with the enzyme linked to the antibody, giving a qualitative visual signal, which may be further quantitated, usually spectrophotometrically, to give an evaluation of the amount of antigen which is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic colour visually detectable with a light microscope. As in an enzyme immunoassay (EIA), the fluorescent-labelled antibody may bind to the first antibody-ST38.2 polypeptide complex. After washing the unbound reagent, the remaining ternary complex is then exposed to light of the appropriate wavelength, and the fluorescence observed indicates the presence of the antigen.

Accordingly, the present invention comprises a test kit for detecting and/or quantitating a wildtype or mutant ST38.2 polypeptide in a sample, comprising the steps of contacting the sample with an antibody as described; and detecting and/or quantitating a polypeptide-antibody complex as an indication of the presence and/or amount of wildtype or mutant ST38.2 polypeptide.

A further embodiment of the present invention comprises ST38.2 receptors. The receptor protein may be isolated by the binding activity of ST38.2 polypeptides to the receptor by methods known in the art, for example as described in International Patent Application WO 9623067. The receptor protein may be modified in a known manner, by attachment of compounds such as polyethylene glycol, or by incorporation in a fusion protein (with other protein sequences such as immunoglobulin sequences).

The present invention is also directed to antagonist/inhibitors of the ST38.2 polypeptide. The antagonist, for example, could be an antibody against the polypeptide which binds to this polypeptide. An example of an inhibitor is a small molecule which binds to and occupies the active site of the ST38.2 polypeptide thereby making the active site inaccessible to the natural substrate such that normal biological activity is prevented. Examples of small molecules include but are not limited to small peptides or peptide-like molecules. Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural polypeptide and thereby prevent the action of ST38.2 polypeptides since the receptor sites are occupied. Accordingly, the antagonists/inhibitors may be used as an anti-inflammation drug useful for the prophylaxis and treatment of disorders correlated with the ST38.2 polypeptides of the present invention, especially with neuroinflammatory diseases of the brain.

The present invention is further directed to inhibiting ST38.2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptides of the present invention, is used to design an antisense RNA oligonucleotide of from about 10 to 40 base pairs in length. A DNA oligonucleotide is designed to be complementary to a region of the gene involved in transcription, thereby preventing transcription and the production of ST38.2 polypeptides. Accordingly, antisense constructs to the ST38.2 polypeptides can be used to antagonize the biological activity of ST38.2 polypeptides, i.e. to treat disorders correlated to ST38.2 polypeptides mentioned below.

Another embodiment of the present invention refers to agonists of ST38.2 polypeptides. The term "agonist" as used herein, is meant to refer to an agent that supplements or potentiates the bioactivity of a functional ST38.2 gene or protein.

Agonists and antagonists of ST38.2 bioactivity may be screened by assays provided by the present invention. By making available purified and recombinant ST38.2 polypeptides, the present invention facilitates the development of assays which can be used to screen for drugs, which are either agonists or antagonists of the normal cellular function of ST38.2 polypeptides. In one embodiment, the assay evaluates the ability of a compound to modulate the biological activity of ST38.2 polypeptides, i.e. to modulate the chemotactic activity and/or the ability to activate leukocytes as mentioned above. A variety of assay forms will suffice and, in light of the present invention, will be comprehended by a skilled artisan.

Assays which are performed in cell-free systems are often preferred as primary screens. Accordingly, in an exemplary screening assay of the present invention, the compound of interest (suspected of being capable of modulating or inhibiting a ST38.2 polypeptide) is contacted with ST38.2 proteins and the biological activity of the ST38.2 polypeptides may be determined as mentioned above, i.e. by determination of the chemotactic activity and/or the ability to activate leukocytes. In addition to cell-free assays, the availability of recombinant ST38.2 polypeptides facilitates the generation of cell-based assays for identifying small molecule agonists/antagonists and the like.

A variety of diseases or conditions caused by inflammatory processes or by immune reactions are associated with ST38.2 polypeptides, especially with clinical recruitment and activation of inflammatory cells including activation of resident immune competent cells related to neuroinflammatory processes, autoimmune diseases (e.g. multiple sclerosis), stroke, ischemia, rheumatoid arthritis and infective diseases, especially meningitis, encephalitis, etc.

Treatment with antibodies or antagonist which inhibit ST38.2 bioactivity may therefore be used to effectively suppress neuroinflammatory or immune responses described above.

The present invention also includes diagnostic and prognostic methods and the corresponding test kits. In an exemplary embodiment, there is provided a nucleic acid composition comprising an oligonucleotide probe including a region of nucleotide sequence which is capable of hybridizing to a sense or antisense sequence of an ST38.2 nucleic acid, such as represented by SEQ ID NO: 1, or naturally occurring mutants thereof, or 5' or 3' flanking sequences or intronic sequences naturally associated with the subject ST38.2 genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine RNA transcript levels. In certain embodiments, detection of the lesion comprises utilizing the polymerase chain reaction. The method includes the steps of (a) collecting a sample of cells from a patient, (b) isolating nucleic acid from the cells of the sample, (c) contacting the nucleic acid sample with one or more primers which specifically hybridize to a ST38.2 gene under conditions such that hybridization and amplification of the ST38.2 gene (if present) occurs, and (d) detecting the presence or absence of an amplification product, or detecting the size or nucleotide changes of the amplification product to a control sample. It is anticipated that PCR and/or LCR may be desirable to use as a preliminary amplification step. Accordingly, the invention provides a test kit for detecting and/or quantitating a wildtype or mutant ST38.2 nucleic acid molecule in a sample, comprising the steps of contacting the sample with a nucleic acid molecule mentioned above; and detecting and/or quantitating the label as an indication of the presence and/or amount of a wildtype or mutant ST38.2 nucleic acid molecule.

This invention includes pharmaceutical compositions comprising a pharmaceutically acceptable carrier and an effective amount of a ST38.2 polypeptide and/or an antibody as defined above. The pharmaceutical composition may further contain one or more of the following compounds: other chemokines, cytokines and/or antagonists thereof. In addition, the present invention relates to a compound prepared by any of the processes mentioned above.

The invention further includes the above compounds for use as therapeutically active substances and for use in the treatment of inflammatory or immune responses. In addition, the invention comprises the use of the above compounds for the manufacture of a medicament, especially for a medicament for the treatment of inflammatory or immune responses.

Pharmaceutically acceptable formulations of ST38.2 and/or the antibodies in connection with this invention can be made using formulation methods known to those of ordinary skill in the art. These formulations can be administered by standard routes. In general, the formulations may be administered parenterally (e.g., intravenous, subcutaneous or intramuscular) with topical, transdermal, oral, or rectal routes also being contemplated. In addition, the formulations may be incorporated into biodegradable polymers allowing for sustained release of ST38.2 and/or the antibodies, the polymers being implanted in the vicinity of where drug delivery is desired. The biodegradable polymers and their use are described, for example, in detail in Brem et al. (1991) J. Neurosurg. 74, 441–446. The dosage of ST38.2 and/or the antibodies will depend on the condition being treated, the particular compound, and other clinical factors such as weight and condition of the human or animal and the route of administration of ST38.2 and/or the antibodies. It is to be understood that the present invention has application for both human and veterinary use. For parenteral administration of a ST38.2 polypeptide to humans, a dosage of between approximately 0.1–100 μg/kg body weight, preferably between approximately 0.1–10 μg/kg 1 to 3 times a week administered intravenously or subcutaneously according to different injection protocols is generally sufficient. For parenteral administration of a corresponding antibody to humans, a dosage of between approximately 0.1–100 μg/kg body weight, preferably between approximately 0.1–10 μg/kg 1 to 3 times a week according to different injection protocols is generally sufficient. It will however be appreciated that the upper and lower limit given above can be exceeded when this is found to be indicated.

The formulations include those suitable for parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association ST38.2 and the pharmaceutical carrier(s) or excipient(s). In general, the formulations are prepared by uniformly and intimately bringing into association the ST38.2 with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, seated ampoules and vials, and may be stored in a freeze-dried (lyophilized) conditions requiring only the addition of the sterile liquid carrier, for example, water for injections, immediately prior to use.

Preferred unit dosage formulations are those containing a daily dose or unit, daily sub-dose, as herein above recited, or an appropriate fraction thereof, of the administered ingredient.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talk or stearic acid or salts thereof.

Suitable excipients for use with soft gelatine capsules include for example vegetable oils, waxes, fats, semi-solid or liquid polyols etc. For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols. The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

This invention will become better understood by reference to the following examples, which are included herein for purpose of illustration only and are not intended to be limiting.

EXAMPLES

Example 1

Animal Models and RNA Isolation

Middle cerebral artery occlusion (MCAO) was performed according to Tamura et al. (1981, J. Cereb. Blood Flow Metab. 1:53–60) in Fisher 344 rats (n=2–3) (BRL, Füllingsdorf) under isoflurane anesthesia. The left MCA was coagulated by bipolar diathermy from its origin to the lateral olfactory tract. MCAO-treated rats (n=2–3) were sacrificed at the indicated timepoints and the ischemic cortices were dissected in (A) infarct core, situated in the parietal, gustatory, agranular insular and cranial temporal cortex, and (B) part of the caudal border area of the infarction situated mostly in the caudal temporal and cranio-ventral occipital cortex located. The corresponding contralateral non-ischemic tissue (c) and tissue from untreated rats served as controls. The infarct core developed pan-necrosis within two days at the latest, whereas the caudal border area included variable amounts of infarct core, tissue with scattered neuronal necrosis neighboring the core and unlesioned tissue as judged by Nissl staining.

Passive experimental allergic panencephalomyelitis (EAP) was induced in Lewis rats (Animal breeding facility of Max-Planck-Institute for Psychiatry, Martinsried) as previously described (Kojima et al. (1994) 180:817–829). Briefly, one group of rats (n=2) received $10^7$ S100 beta-specific T cells which provoked an inflammatory response in the central nervous system but only minimal neurologic dysfunction. A second group received S100 beta-specific T cells followed by a single dose of anti-MOG antibody (Mab 8–18C5, 4 mg/rat, i.p.) at day four after the cell transfer. This group showed an increased infiltration of inflammatory cells and clinical signs of disease such as tail limbness became manifest at day six. Histologically, foci of demyelination arranged around the infiltrates can be detected. When indicated animals were treated with a single intraperitoneal injection of TNFRp55-IgG1 (European Patent Application No. 417 563) at a dose of 10 mg/kg at day 2 which prevented cell infiltration in the CNS and clinical symptoms (Klinkert et al. (1997) 97:163–168). Animals were sacrificed at the indicated timepoints, perfused and total brain tissue was harvested. All tissues were immediately snap-frozen in liquid nitrogen and stored at −80° C. Total RNA was extracted from the tissue samples with RNAzol (AMS) according to the manufacturer's instructions.

Example 2

Cell Populations

Primary mouse astrocyte cultures were prepared as previously described (Fischer et al. (1982) Neurosci. Lett. 29:297–302); Liang & Pardee (1992) Science 257:967–971). In brief, astrocyte precursors were isolated from early postnatal cerebella and cultivated in a serum-free medium (DMEM, 10 ng/ml EGF, 10 µg/ml insulin, 10 µg/ml 100 µg/ml transferrin, 1 g/l BSA, 10 U/ml penicillin, 100 µg/ml streptomycin). Prior to stimulation cells were differentiated for 2–3 days by replacing the serum-free medium with medium containing 10% FCS. After differentiation more than 98% of the cells stained positive for glial fibrillary acid protein (GFAP). Peripheral blood mononuclear cells were isolated from rat blood by Ficoll-Hypaque gradient centrifugation and cultured in DMEM medium. A lymphocyte-enriched cell population was obtained by negative selection of a rat splenocyte suspension using a T-cell enrichment column (R&D systems).

Example 3

Differential Display

Differential display analysis was carried out as previously reported (Liang et al., loc. cit.; Utans et al. (1994) Proc. Natl. Acad. Sci. USA 91:6463–6467) with the following modifications. Total RNAs (2.5 µg) obtained from infarct core or border zone tissue of rats sacrificed at several time points after MCAO (one animal per timepoint) and of untreated control animals was reverse transcribed to first strand cDNA with 200 units of Superscript reverse transcriptase (Gibco BRL) in the presence of 0.5 µg oligo(dT) primer containing an Xba1 restriction site (5'-GCTCTAGAT$_{16}$-3') (SEQ ID NO:4) and 100 µM dNTP mixture for 60 min at 37° C. 1/20 volume of the cDNAs were amplified by PCR in the presence of 1 µCi [α$^{33}$P]dATP on a Biometra thermal cycler. PCR parameters were 40 cycles of denaturation at 94° C. for 45 sec, annealing at 30° C. for 2 min, and extension at 72° C. for 45 sec. The reaction mixes included 1 µM of an anchored 5' primer containing three repeats of the ATTTA pentamer in combination with 1 µM of the Xba1-T$_{16}$ primer (Asson-Batres et al. (1994) 91:1318–1322). Due to the high A/T content of the ATTTA sequence an anchor of at least six nucleotides (having a GC content of 50–70%) 5' of the (ATTTA)$_3$ sequence is required for stable and efficient hybridization of the primer under the conditions used. Several arbitrary nucleotide combinations have been tested and resulted in a distinct but overlapping set of PCR products. Primer annealing allowed several mismatches to occur which were located primarily in the anchor sequence (up to 4 mismatches) and to a lesser extent in the AUUUA repeat portion (1–3 mismatches). The ST38.2 fragment was identified in a set of reactions amplifying infarct core cDNAs with 5'-GTCTTGTATTTATTTATTTAT-3' (SEQ ID NO:5) primer in combination with the Xba1-T$_{16}$ primer. Radiolabeled PCR amplification products were separated by electrophoresis in denaturing 6% polyacrylamide gels and analyzed by autoradiography. Differentially regulated PCR product bands were recovered from the gel, reamplified and subcloned into the TA-cloning vector pCRII (Invitrogen). Inserts were subjected to automated sequencing on a LI-COR DNA sequencer.

Example 4

Rapid Amplification of 5'-cDNA Ends (5' RACE) and Sequence Analysis

A 5' extended ST38.2 cDNA was obtained by 5' RACE using the marathon cDNA amplification kit (Clontech). PolyA$^+$ RNA prepared from 4 h MCAO border zone tissue served as template for cDNA preparation. Adapters were ligated to the double strand cDNA. ST38.2 gene-specific primers [GSP1 5'-GCTTATTGTTTCCAAGAAGGGCC-3' (SEQ ID NO:6), GSP2 5'-GCGCCCCTCATAGATTGTGGGAA-3') (SEQ ID NO:7)] and adapter-specific primers were used in two subsequent, nested PCR amplifications. The RACE reaction resulted in a prominent PCR product band of about 800 bp that was cloned into vector pCRII (Invitrogen). Several cDNA clones were sequenced on both strands using a LI-COR automated sequencer. DNA homology searches of GenBank and EMBL databases and the analysis of the nucleotide and the predicted amino acid sequence were performed with the GCG software package (Genetics Computer Group, Wisconsin). Hydrophilicity plots were generated with the Kyte-Doolittle algorithm using a window size of 7. The predicted cleavage site of the mature form of ST38.2 were obtained through the Signalp server at www.cbs.dtu.dk/services/signalP/ (Nielsen et al. (1997) Protein Engineering, 10:1–6).

Example 5

Northern and Genomic Southern Blot Analysis

For Northern blot analysis 20 µg of total RNA were separated on 1.2% formaldehyde agarose gels, transferred to nylon membranes (Genescreen Plus) and hybridized with specific probes generated by labeling the ST38.2 differential display cDNA fragment or full length ST38.2 cDNA with [α-$^{32}$P]dCTP using a random priming kit (Pharmacia). Washing conditions were 0.2×SSC, 0.1% SDS at 42° C. To control for RNA loading, blots were stripped and rehybridized with a probe for glyceraldehyde-3-phosphate dehydrogenase (G3PDH).

Figure 6:
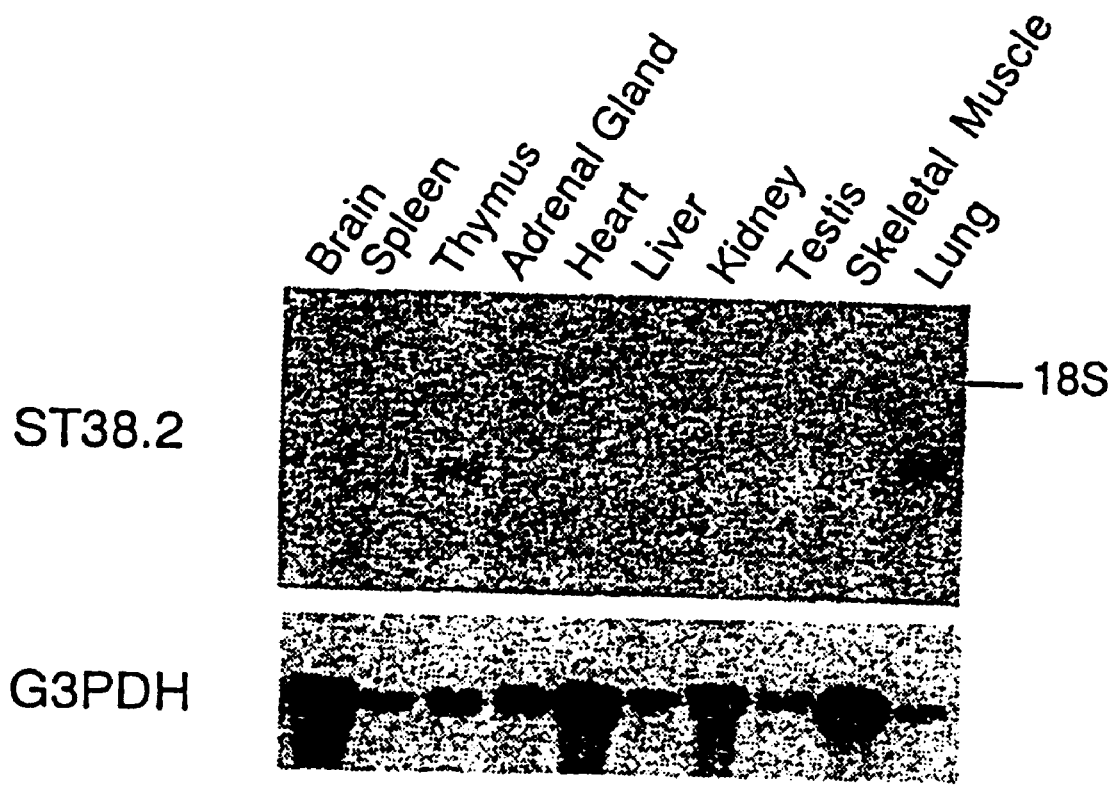
FIG. 6: Northern blot analysis of rat organs. Total RNA was isolated from the indicated rat organs and hybridized with a $^{32}$P-labeled ST38.2 cDNA. ST38.2 transcripts of 0.8 kb are visible in thymus and lung. RNA loading was demonstrated by rehybridizing the blot with a probe for G3PDH.

Blots were prepared with total RNA isolated from several rat organs and hybridized with a ST38.2 cDNA probe. ST38.2 transcripts were found to be expressed at low levels in thymus and lung (FIG. 6). No expression could be detected in any of the other tissues tested including normal brain tissue.

Mouse, rat and human genomic DNA was isolated and digested with restriction endonucleases as indicated. Transfer to nylon membranes and hybridization to full length ST38.2 cDNA probes was performed as described above. Low stringency (2×SSC, 0.1% SDS at 60° C.) and high stringency (0.1×SSC, 0.1% SDS at 65° C.) washing steps were performed. Blots were analyzed using a Phosphorimager System (Molecular Dynamics). In addition blots were exposed to Kodak XAR film.

Figure 3:
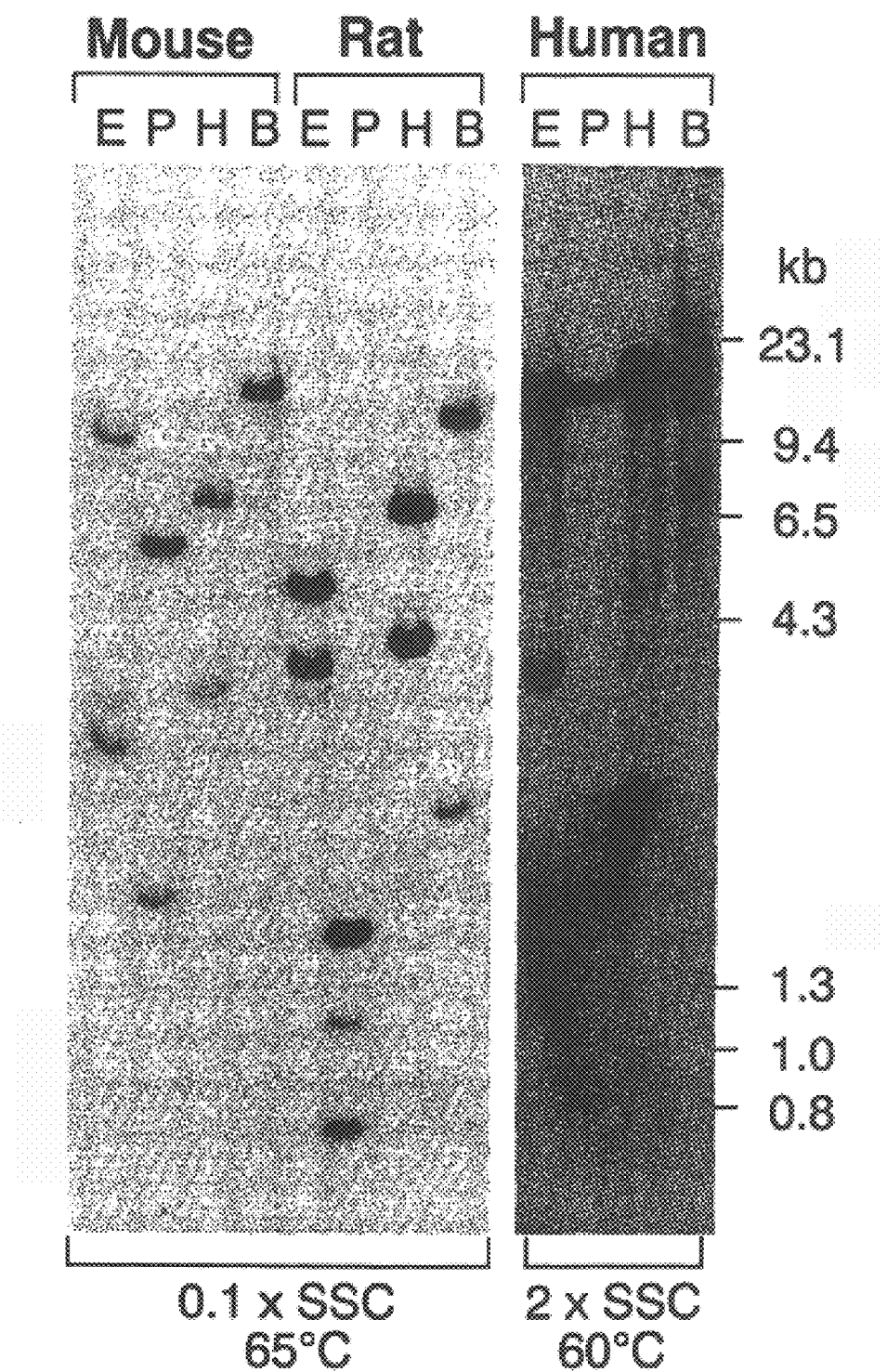
FIG. 3: Genomic Southern Analysis. Mouse, rat and human genomic DNA was digested with the indicated restriction enzymes, transferred to membranes and hybridized with the complete $^{32}$P-labeled rat ST38.2 cDNA. Conditions of the low and high stringency washing steps are mentioned in Example 5.

Rat, mouse and human genomic DNA was digested with four different restriction enzymes and hybridized with the complete $^{32}$P-labeled rat ST38.2 cDNA probe (FIG. 3). The ST38.2 cDNA recognized rat and mouse genomic DNA under high stringency conditions (0.1×SSC/0.1% SDS, 65° C.) whereas hybridization to human genomic DNA was only apparent under low stringency conditions (2×SSC/0.1% SDS, 60° C.). This demonstrates that sequence conservation is high between rat and mouse but reduced to a lower degree in human DNA. The hybridization pattern observed in all three species suggests that ST38.2 is encoded by a single copy gene.

Example 6
Reverse Transcriptase-PCR Assays

Total RNA was reverse transcribed with Oligo(dT) primers using Superscript reverse transcriptase as suggested by the manufacturer's manual (Gibco/BRL). To confirm the upregulation of the ST38.2 differential display fragment by RT-PCR we used 5' primer F1 (5'-TTCCCACAATCTATGAGG-3') (SEQ ID NO:8) and 3' primer R1 (5'-GTTCTTCTGTGTGCTTAATTG-3') (SEQ ID NO:9) which are located within the 3' cDNA fragment identified by differential display and generate a 129 bp PCR product. All other RT-PCR assays were performed with 5' primer F2 (5'-TTGACTGCTGCCTCACGTACAC-3') (SEQ ID NO:10) and 3' primer R2 (5'-GACCTGATTTGTGTCCCAGTGG-3') (SEQ ID NO:11) which amplify a 320 bp PCR product including parts of the open reading frame. Reaction conditions included 0.5 $\mu$M 5' and 3' primer 200 $\mu$M dNTPs 10 mM Tris-HCl (pH 8.3), 50 mM KCl, 1.5 mM MgCl$_2$ and 1 U Taq DNA polymerase in a total volume of 25 $\mu$l. The thermal cycling parameters were denaturation at 94° C. for 20 sec, annealing at 55° C. (primer pair F1/R1) or 60° C. (F2/R2) for 30 sec, and extension at 72° C. for 60 sec (with a final extension of 7 min at the end of all cycles). PCR products were separated on agarose gels and visualized by ethidium bromide staining. When indicated PCR products were transferred to nylon membranes and visualized by chemoluminescent detection using a biotin-labelled ST38.2 probe (Southern-Light Kit, Tropix).

For semiquantitative reverse-transcriptase PCR assays, cDNA synthesis was completed with random primers (2.5 $\mu$g of total RNA per reaction). PCR amplifications were done in triplicates using primer pair F2/R2 and the reaction conditions described above with the exception that dUTP was replaced with digoxigenin(DIG)-UTP in the reaction mix. PCR products were quantified using the PCR ELISA kit (Boehringer). In brief, PCR products were denatured, hybridized to an internal biotin-labeled oligonucleotide (5'-GGCTGTGTCCAATTCCATCCCAG-3') (SEQ ID NO:12) and captured on a streptavidin-coated microtiter plate. Detection was performed with an anti-DIG-peroxidase antibody conjugate and the substrate luminol resulting in a chemoluminescent signal that was measured in a luminescent counter. To identify the optimal PCR conditions for accurate measurement of transcript levels, we established the linear assay ranges with respect to cycle number and starting template concentration. Measurement of ST38.2 transcript levels was then completed within these ranges; 30–32 cycles and cDNA dilution of 1:3 (0.42 $\mu$l per reaction). PCR amplification with G3PDH, an ubiquitously expressed gene, was used as control to assess variations in total RNA or cDNA lading between samples. Corrected ST38.2 values were derived by dividing the measured amplified product value by the mean of the G3PDH value obtained for that cDNA and expressed in arbitrary units.

Figure 4:
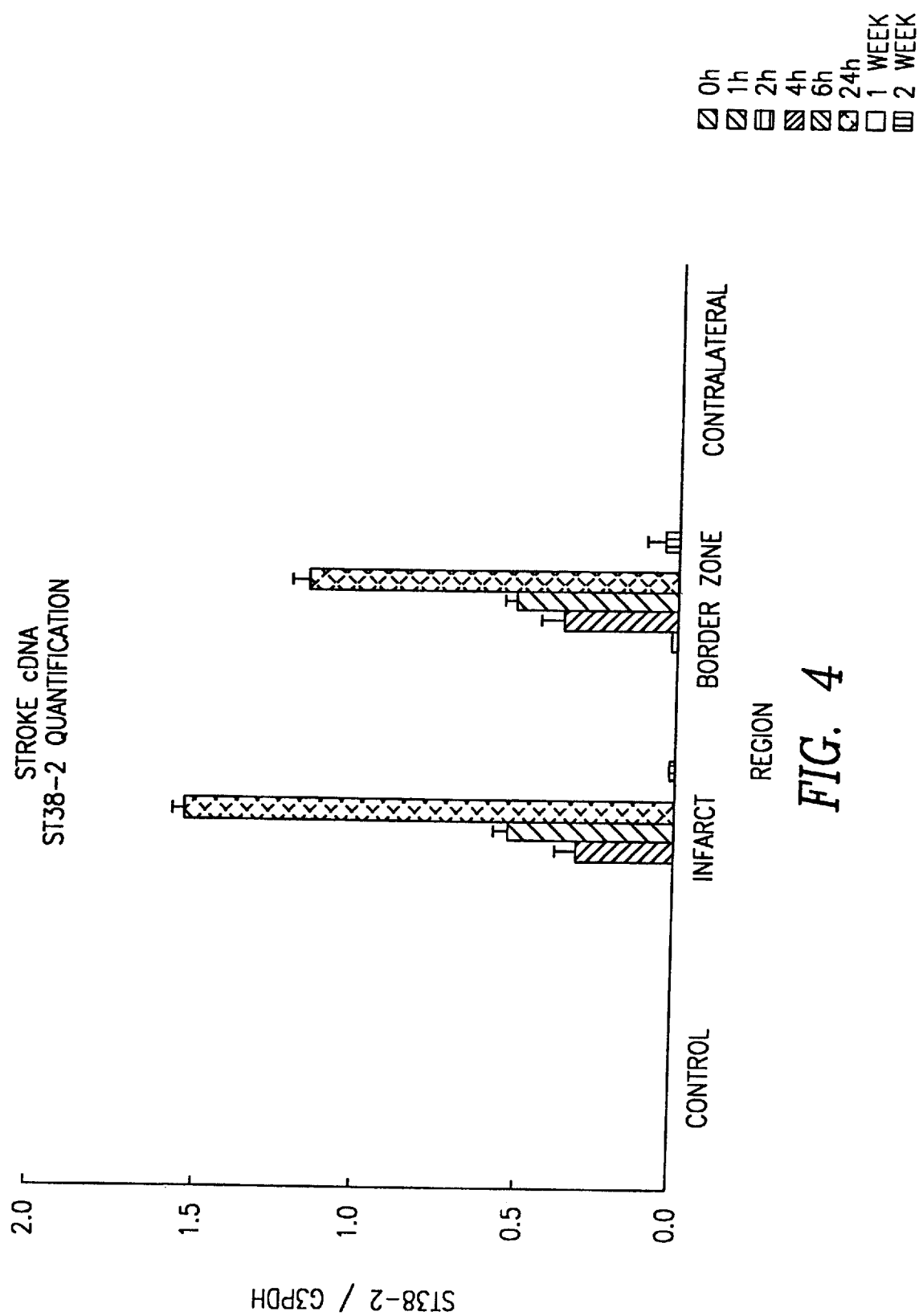
FIG. 4: Semiquantitative RT-PCR analysis of ST38.2 expression in MCAO tissue. PCR reactions were performed under optimized conditions in which amplified product was proportional to the initial target mRNA (30 cycles, cDNA dilutions of 1:3) with ST38.2-specific primers (F2/B2) amplifying the region between nt 138 and 458. PCR products were quantified by PCR ELISA. Corrected values were derived by normalizing ST38.2 values against those for the control gene, G3PDH, and are shown in relative units. Data are plotted as means +/−SEM and represent three separate PCR analyses.

The above conditions were then used to compare relative differences in ST38.2 expression between cDNA samples prepared from control tissue, infarct core, border zone and contralateral tissue (FIG. 4). A transient increase in expression over time in infarct core and border zone was detected whereas no expression was seen in untreated, sham-operated or contralateral tissue. Expression levels were increased 3-fold after 4 h, 6-fold after 6 h and peaked at 24 h with a 12 to 15-fold increase in both infarct and border zone. Seven or 14 days after ischemic injury ST38.2 expression was reduced to background levels.

Figure 5A:
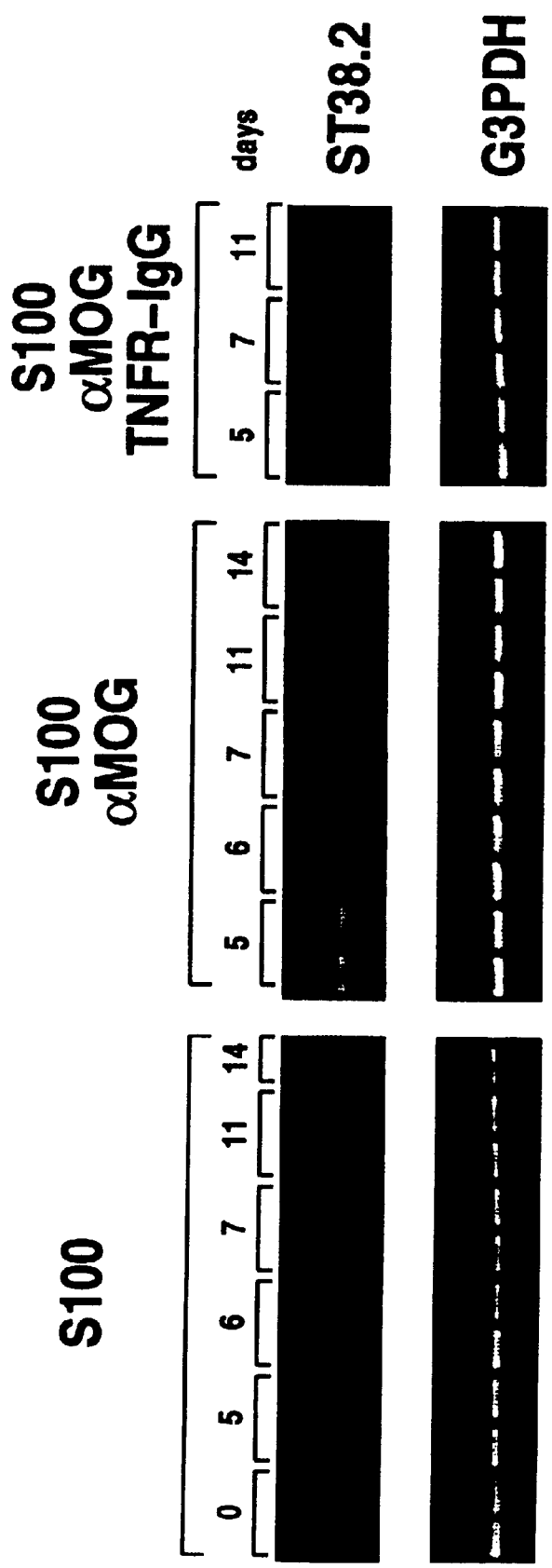
FIG. 5A: Upregulation of ST38.2 transcripts in a rat model of experimental allergic panencephalomyelitis. Untreated animals (d 0), animals receiving T cells reactive against S100 beta protein (S100) or a combination of S100-beta T cells and anti-MOG antibodies were harvested at the indicated time points after MCAO and total RNA was isolated from brain tissue of two individual animals each. When indicated animals were injected with a TNFRp55-IgG fusion protein. Total RNAs were reverse transcribed into cDNAs and PCR amplified with ST38.2 specific primers F2/B2 for 35 cycles. PCR reactions were analyzed on ethidium-stained agarose gels.
Figure 5B:
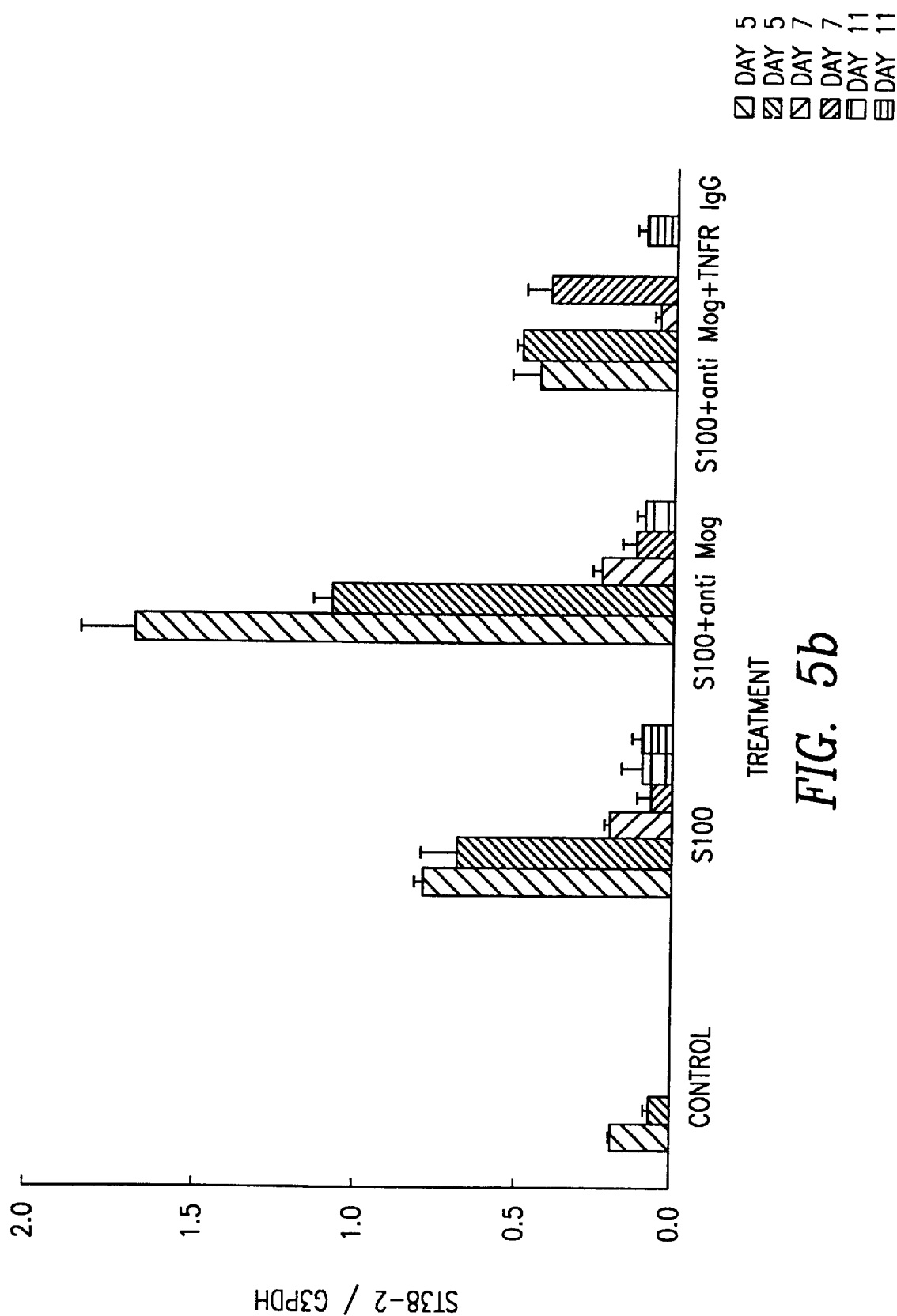
FIG. 5B: Upregulation of ST38.2 transcripts in a rat model of experimental allergic panencephalomyelitis. To get a more quantitative assessment of the induction levels of ST38.2 transcription in the different disease stages, a semi-quantitative RT-PCR analysis was performed. A 7 to 8-fold increase in ST38.2 transcript levels compared to levels in control tissue was seen at day 5 in the CNS of animals transferred with S100beta-specific T-cells, whereas 11 and 17 fold increases were seen in animals receiving T cells and anti-MOG antibodies. TNFRp55IgG treatment reduced the induction to 4-fold.

Example 7
Induced ST38.2 Expression in Experimental Allergic Panencephalomyelitis To determine whether increased ST38.2 expression may have a general role in neuroinflammation, ST38.2 transcript levels in a rat model of experimental autoimmune panencephalomyelitis (EAP) was analyzed. EAP was induced by transfer of T-cells specific for the astrocyte S100beta protein and subsequent injection of anti-MOG antibodies (Max-Planck-Institute for Psychiatry, Martinsried) (Kojima et al., loc. cit.). Histopathology of this model revealed that recruitment of inflammatory cells into the perivascular space of the CNS starts at day four, is high at day five and decreases at later time points. Clinical disease in parallel to tissue damage and demyelination develops in animals injected with anti-MOG antibodies, is most prominent at days 6 and 7, and leads to ultimate recovery. A recent study demonstrated that the development of inflammatory lesions and of the clinical symptoms can be prevented by treatment with an TNF-receptor-p55IgG fusion protein (Klinkert et al., loc. cit.). The expression of ST38.2 transcripts in CNS tissue was examined by RT-PCR at several time points after transfer of S100beta-specific T-cells alone, after transfer of S100beta-specific T-cells combined with subsequent administration of anti-MOG antibodies, and in TNFRp55IgG treated animals (FIG. 5A). In animals injected with S100beta-specific T-lymphocytes only, the transcription of ST38.2 mRNA in the CNS was upregulated at day 5 and returned to background levels at day 6 and later time points. When animals received anti-MOG antibodies in addition to the T-cell transfer the increase in ST38.2 transcript levels at day 5 was substantially more pronounced, but again ST38.2 mRNA levels started to decrease as soon as day 6 and remained low until day 14. Treatment with TNFRp55IgG fusion protein significantly reduced the induction of ST38.2 transcription observed at day 5. To get a more quantitative assessment of the induction levels of ST38.2 transcription in the different disease stages, a semi-quantitative RT-PCR analysis was performed (FIG. 5B). A 7 to 8-fold increase in ST38.2 transcript levels compared to levels in control tissue was seen at day 5 in the CNS of animals transferred with S100beta-specific T-cells, whereas 11 and 17 fold increases were seen in animals receiving T cells and anti-MOG antibodies. TNFRp55IgG treatment reduced the induction to 4-fold.

Example 8
Expression in In Vitro Cell Populations

To elucidate which cell type(s) are the source of ST38.2 during CNS inflammation the inducibility of ST38.2 transcription was investigated in several in vitro cell populations by RT-PCR. In primary mouse astrocytes it was found that ST38.2 expression was substantially induced 1 h and 3 h after stimulation with TNF alpha (FIG. 7A). Furthermore, also peripheral blood mononuclear cells can be stimulated to express ST38.2 transcripts by activation with LPS for 2 h (FIG. 7B). Stimulation of a splenocyte suspension with Concanavalin A resulted in elevated ST38.2 transcript levels after a 18 hour incubation period.

Example 9
Expression of Recombinant ST38.2 Proteins

Figure 8:
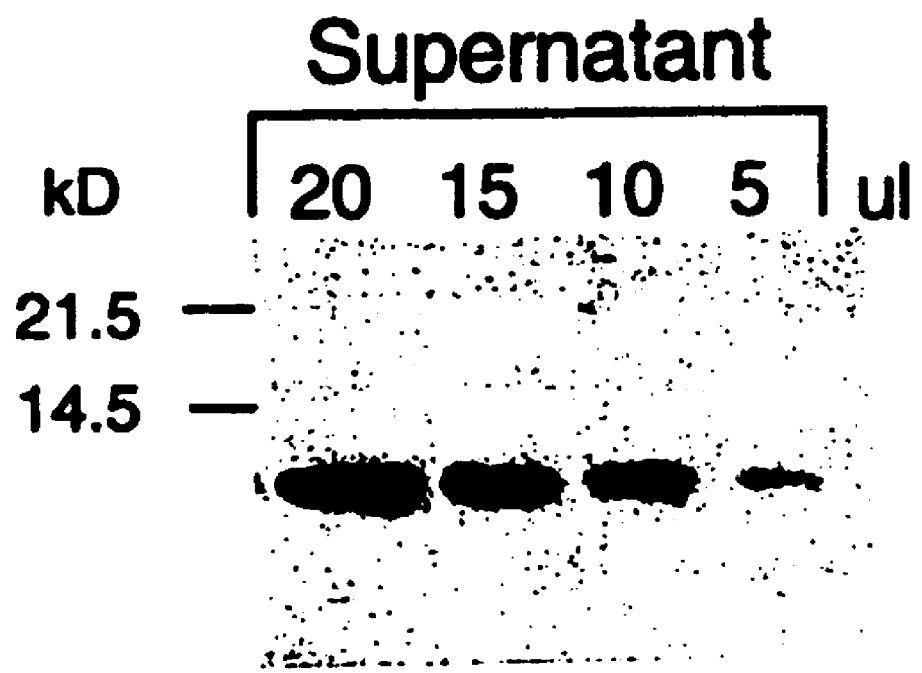
FIG. 8: Expression of recombinant rat ST38.2 protein in eukaryotic cells. The rat ST38.2 cDNA containing the open reading frame and a C-terminal FLAG-epitope was cloned into the eukaryotic expression vector pREP7 (Invitrogen) and transiently transfected into HEK 293/EBNA cells. The secreted ST38.2 protein was detected in the medium supernatant harvested at day 5 after transfection by Western blot analysis using an anti-FLAG antibody (at a dilution of 1:1000) (Eastman Kodak).

The ST38.2 cDNA containing the open reading frame and a C-terminal FLAG-epitope was cloned into the eukaryotic expression vector pREP7 (anvitrogen) and transiently transfected into HEK 293/EBNA cells. The secreted ST38.2 protein was detected in the medium supernatant harvested at day 5 after transfection by Western blot analysis using an anti-FLAG antibody (at a dilution of 1:1000) (Eastman Kodak) (FIG. 8).

Figure 9A:
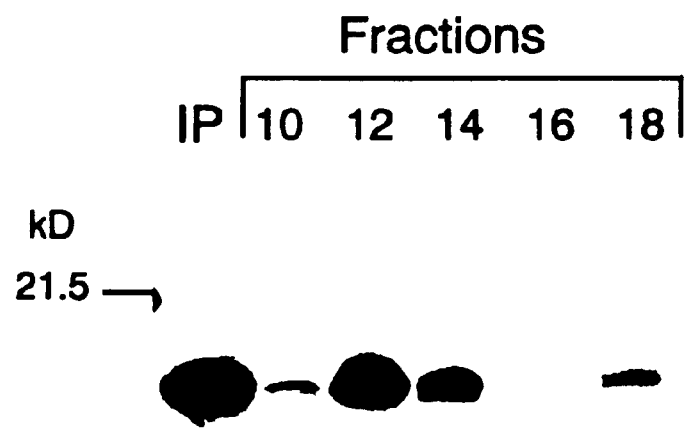
FIG. 9A: Purification of rat ST38.2 protein on an anti-FLAG affinity column (Eastman Kodak). 100 ml of medium supernatant were applied to a 1 ml anti-FLAG affinity column and eluted with 0.1 M glycine pH 3.5 in 0.5 ml fractions. ST38.2-FLAG protein was detected in the input and the indicated fractions of the eluate (10 µl) by Western blotting using an anti-FLAG antibody.
Figure 9B:
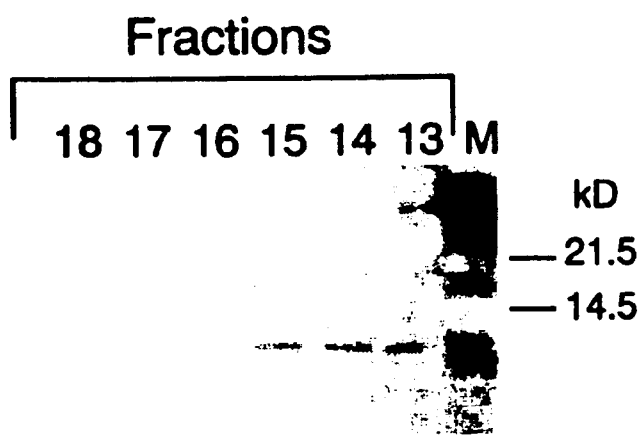
FIG. 9B: Same as FIG. 9A except that ST38.2-FLAG protein was detected by SDS-PAGE and silver staining.

For purification of the recombinant protein, 100 ml of medium supernatant were applied to a 1 ml anti-FLAG affinity column and eluted with 0.1 M glycine pH 3.5 in 0.5 ml fractions. ST38.2-FLAG protein was detected in the input and the indicated fractions of the eluate (10 µl) by Western blotting using an anti-FLAG antibody (FIG. 9 A) or by SDS-PAGE and silver staining (FIG. 9B).

The purified ST38.2-FLAG protein was used to obtain the N-terminal amino acid sequence:

(SEQ ID NO: 13)

1                                12

A-S-N-F-D-X*-X-L-T-Y-T-T-K

* Cysteins cannot be detected without prior derivatisation. The result confirms tat cleavage of the signal sequence occurs at the predicted cleavage site after amino acid 25 (SEQ ID NO: 2)

What is claimed is:

1. An isolated nucleic acid molecule comprising the sequence of nucleotides 53 to 340 of SEQ ID NO:1.

2. At least one isolated nucleic acid molecule consisting of the sequence SEQ ID NO:1.

3. An expression vector, comprising the nucleic acid molecule of claim 1 operably linked to a transcriptional regulatory sequence.

4. A host cell transfected with the expression vector of claim 3.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
       (A) LENGTH: 797 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION:53..340

(xi) SEQUENCE DESCRIPTION: SEQ ID NO: 1:

```
CAGCAGGGCA CTGGGTACCC AGCACTGAGC AGATCAATTC CTGGAGCTGA GA ATG       55
                                                          Met
                                                          1

GCC TGC AAG CAT CTG CCC TTC CTG GCT TTG GCG GGG GTA CTG CTG GCT   103
Ala Cys Lys His Leu Pro Phe Leu Ala Leu Ala Gly Val Leu Leu Ala
             5                  10                  15

TAC CTC TGC AGC CAG TCA GAA GCA GCA AGC AAC TTT GAC TGC TGC CTC   151
Tyr Leu Cys Ser Gln Ser Glu Ala Ala Ser Asn Phe Asp Cys Cys Leu
         20                  25                  30

ACG TAC ACA AAG AAC GTG TAT CAT CAT GCG AGA AAT TTT GTG GGT TTC   199
Thr Tyr Thr Lys Asn Val Tyr His His Ala Arg Asn Phe Val Gly Phe
     35                  40                  45

ACA ACA CAG ATG GCC GAC GAA GCT TGT GAC ATT AAT GCT ATC ATC TTT   247
Thr Thr Gln Met Ala Asp Glu Ala Cys Asp Ile Asn Ala Ile Ile Phe
 50                  55                  60                  65

CAC CTG AAG TCG AAA AGA TCC GTG TGC GCT GAC CCA AAG CAG ATC TGG   295
His Leu Lys Ser Lys Arg Ser Val Cys Ala Asp Pro Lys Gln Ile Trp
                 70                  75                  80

GTG AAA AGG ATT TTG CAC CTC CTC AGC CTA AGA ACC AAG AAG ATG       340
Val Lys Arg Ile Leu His Leu Leu Ser Leu Arg Thr Lys Lys Met
                 85                  90                  95

TAAAAACGGA TGCTTTTCTG GGATGGAATT GGACACAGCC CAAGGAGGAA ATGATCACAG  400

CTGGGGTTGG AGGTTTCACC TGCACATCAC TGCACAGACC TGATTTGTGT CCCAGTGGTC  460

TTGTCCAATG GATGAAGTTG ATTCATATTG CATCATAGTG TGTCATATTT AAGCTCATAT  520
```

```
TAGAGTTAAG TTGTATTTTG TGTTATTTAT AGATCCGAAT TTTCTATGTT TAGCTATTTA      580

ATGTTAATTT CCCACAATCT ATGAGGGGCG CTTAGTAGAA GGTTCAATAT TATGTTTAAG      640

GCAGTAAGTT TATATGGCCC TTCTTGGAAA CAATAAGCTA TTGTAAAAAT ATTTAATGTT      700

CTTCTGTGTG CTTAATTGTT TCTTAAATTG ATACGATTTA CTTATAAAAC AGAAAGGAAT      760

TATAAGAATA TATTGAAAAT AAAAGAACTG AAAGGCA                              797
```

(2) INFORMATION FOR SEQ ID NO: 2:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Cys Lys His Leu Pro Phe Leu Ala Leu Ala Gly Val Leu Leu
 1               5                  10                  15

Ala Tyr Leu Cys Ser Gln Ser Glu Ala Ala Ser Asn Phe Asp Cys Cys
                20                  25                  30

Leu Thr Tyr Thr Lys Asn Val Tyr His His Ala Arg Asn Phe Val Gly
            35                  40                  45

Phe Thr Thr Gln Met Ala Asp Glu Ala Cys Asp Ile Asn Ala Ile Ile
    50                  55                  60

Phe His Leu Lys Ser Lys Arg Ser Val Cys Ala Asp Pro Lys Gln Ile
65                  70                  75                  80

Trp Val Lys Arg Ile Leu His Leu Leu Ser Leu Arg Thr Lys Lys Met
                85                  90                  95
```

(2) INFORMATION FOR SEQ ID NO: 3:

(i) SEQUENCE CHARACTERISTICS:
        (A) LENGTH: 71 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 3:

```
Ala Ser Asn Phe Asp Cys Cys Leu Thr Tyr Thr Lys Asn Val Tyr His
 1               5                  10                  15

His Ala Arg Asn Phe Val Gly Phe Thr Thr Gln Met Ala Asp Glu Ala
                20                  25                  30

Cys Asp Ile Asn Ala Ile Ile Phe His Leu Lys Ser Lys Arg Ser Val
            35                  40                  45

Cys Ala Asp Pro Lys Gln Ile Trp Val Lys Arg Ile Leu His Leu Leu
    50                  55                  60

Ser Leu Arg Thr Lys Lys Met
65                  70
```

(2) INFORMATION FOR SEQ ID NO: 4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 4:

GCTCTAGAT                                                                                       9

(2) INFORMATION FOR SEQ ID NO: 5:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "primer"

(xi) SEQUENCE DESCRIPTION: SEQ ID NO: 5:

GTCTTGTATT TATTTATTTA T                                                                        21

(2) INFORMATION FOR SEQ ID NO: 6:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "primer"

(xi) SEQUENCE DESCRIPTION: SEQ ID NO: 6:

GCTTATTGTT TCCAAGAAGG GCC                                                                      23

(2) INFORMATION FOR SEQ ID NO: 7:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "primer"

(xi) SEQUENCE DESCRIPTION: SEQ ID NO: 7:

GCGCCCCTCA TAGATTGTGG GAA                                                                      23

(2) INFORMATION FOR SEQ ID NO: 8:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "primer"

(xi) SEQUENCE DESCRIPTION: SEQ ID NO: 8:

TTCCCACAAT CTATGAGG                                                                            18

(2) INFORMATION FOR SEQ ID NO: 9:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid -continued

```
        (A) DESCRIPTION:    /desc = "primer"

(xi) SEQUENCE DESCRIPTION: SEQ ID NO: 9:

GTTCTTCTGT GTGCTTAATT G                                             21

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer"

(xi) SEQUENCE DESCRIPTION: SEQ ID NO: 10:

TTGACTGCTG CCTCACGTAC AC                                            22

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer"

(xi) SEQUENCE DESCRIPTION: SEQ ID NO: 11:

GACCTGATTT GTGTCCCAGT GG                                            22

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer"

(xi) SEQUENCE DESCRIPTION: SEQ ID NO: 12:

GGCTGTGTCC AATTCCATCC CAG                                           23

(2) INFORMATION FOR SEQ ID NO: 13:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 13:

Ala Ser Asn Phe Asp Xaa Xaa Leu Thr Tyr Thr Thr Lys
1               5                   10
```